US007276488B2

(12) United States Patent
Kingsman et al.

(10) Patent No.: US 7,276,488 B2
(45) Date of Patent: *Oct. 2, 2007

(54) VECTOR SYSTEM

(75) Inventors: Alan J. Kingsman, Oxford (GB); Christopher R. Bebbington, Oxford, CA (US); Miles W. Carroll, Oxford (GB); Fiona M. Ellard, Oxford (GB); Susan M. Kingsman, Oxford (GB); Kevin A. Myers, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 90 days.

This patent is subject to a terminal disclaimer.

(21) Appl. No.: 10/060,585

(22) Filed: Jan. 29, 2002

(65) Prior Publication Data

US 2003/0083290 A1    May 1, 2003

Related U.S. Application Data

(63) Continuation-in-part of application No. PCT/GB00/04317, filed on Nov. 13, 2000, and a continuation-in-part of application No. 09/445,375, filed on Mar. 21, 2000, now Pat. No. 6,852,703.

(30) Foreign Application Priority Data

| Jun. 4, 1997 | (GB) | 9711579.4 |
| Jun. 20, 1997 | (GB) | 9713150.2 |
| Jul. 4, 1997 | (GB) | 9714230.1 |
| Nov. 18, 1999 | (WO) | PCT/GB99/03859 |
| Feb. 15, 2000 | (GB) | 0003527.9 |
| Mar. 2, 2000 | (GB) | 0005071.65 |

(51) Int. Cl.
*A61K 48/00* (2006.01)

(52) U.S. Cl. ............................... 514/44; 424/178.1
(58) Field of Classification Search ................ 514/44; 424/93.1, 178.1; 435/320.1
See application file for complete search history.

(56) References Cited

U.S. PATENT DOCUMENTS

| 4,997,913 | A |   | 3/1991 | Hellstrom et al. |
| 5,559,099 | A |   | 9/1996 | Wickham et al. |
| 5,591,624 | A |   | 1/1997 | Barber et al. |
| 5,824,782 | A | * | 10/1998 | Holzer et al. ............ 530/391.1 |
| 5,856,140 | A |   | 1/1999 | Shimamura et al. |
| 5,876,691 | A |   | 3/1999 | Chester et al. |
| 6,348,584 | B1 |  | 2/2002 | Hodgson et al. |
| 6,514,498 | B1 |  | 2/2003 | Antonsson et al. |
| 6,852,703 | B1 |  | 2/2005 | Kingsman |

FOREIGN PATENT DOCUMENTS

| EP | 0336562 A1 | 10/1989 |
| EP | 0 803 574 A2 | 5/1990 |
| WO | WO89/07947 | 3/1989 |
| WO | WO92/11383 A1 | 7/1992 |
| WO | WO92/22653 A1 | 12/1992 |
| WO | WO94/11513 | 11/1993 |
| WO | WO96/15238 | 11/1995 |
| WO | WO96/30504 | 3/1996 |
| WO | WO96/30512 | 3/1996 |
| WO | WO96/34969 | 5/1996 |
| WO | WO97/17090 A1 | 5/1997 |
| WO | WO97/36932 A1 | 10/1997 |
| WO | WO98/55607 A2 | 12/1998 |
| WO | PCT/GB00/04317 A2 | 5/2001 |
| WO | WO01/36486 A2 | 5/2001 |

OTHER PUBLICATIONS

Greco, O. et al. "Cancer gene therapy: delivery, delivery, delivery." Frontiers in Bioscience, 2002, vol. 7, pp. d1516-1524.*

Crystal, R.G. "Transfer of genes to humans: early lessons and obstacles to success." Science, 1995, vol. 270, pp. 404-410.*

Gertsmayer, B. et al. The Journal of Immunology, vol. 158, pp. 4584-4590 (1997).*

Naldini et al (Science, 1996; 272:263-267).*

Anderson, W. French, "Human gene therapy," Nature, vol. 392, Apr. 30, 1998, p. 25-30.

Chamberlain, Ronald S., et al., "Costimulation Enhances the Active Immunotherapy Effect of Recombinant Anticancer Vaccines," Cancer Research, vol. 56, Jun. 15, 1996, p. 2832-2836.

Forsberg, Goran, et al., Identification of Framework Residues in a Secreted Recombinant Antibody Fragment That Control Production Level and Localization in *Escherichia coli*, The Journal of Biological Chemistry, vol. 272, No. 19, May 9, 1997, p. 12430-12436.

Mountain, Andrew, "Gene therapy: the first decade," TIBTECH, vol. 18, Mar. 2000, p. 119-127.

Myers, Kevin A., et al., "Isolation of a cDNA Encoding 5T4 Oncofetal Trophoblast Glycoprotein," The Journal of Biological Chemistry, vol. 269, No. 12, Mar. 25, 1994, p. 9319-9324.

Verma, Inder M., et al., "Gene therapy promises, problems and prospects," Nature, VI. 389, Sep. 18, 1997, p. 239-242.

Walther, Wolfgang, et al., "Viral Vectors for Gene Transfer," Drugs, vol. 2, Aug. 2000, p. 249-271.

Riddell, S.R., et al. "T-cell mediated rejection of gene-modified HIV-specific cytotoxic T lymphocytes in HIV-infected patients", *Nature Medicine* (1996) 2:216-221.

Richter, J., et al. "Clinical gene therapy in hematology: Past and future", *Int. Journal. Hematology* (2001) 73:162-169.

(Continued)

*Primary Examiner*—Jon E. Angell
(74) *Attorney, Agent, or Firm*—Townsend and Townsend and Crew LLP

(57) ABSTRACT

The present invention provides a vector system comprising a nucleotide sequence coding for an antibody. In particular, the present invention relates to the use of such a vector system in a subject, where the nucleotide sequence is expressed in vivo to produce said antibody.

18 Claims, 13 Drawing Sheets

OTHER PUBLICATIONS

Figure 3A:
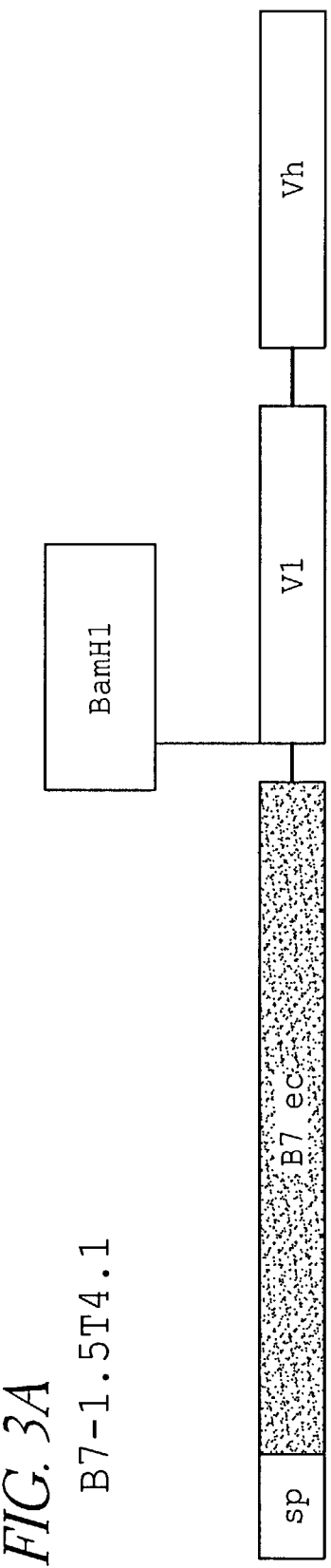

Rieger, et al., *Glossary of Genetics and Cytogenetics, Classical and Molecular*. 4th Ed., Springer-Verlag, Berlin, 1976.

Rudikoff, et al., "Single amino acid substitution altering antigen-binding specificity", *Proc. Natl Acad Sci USA* (1982) 79:1979-1983.

Overbeek, Paul A., "Factors affecting transgenic animal production", *Transgenic Animal Technology* (1994) 96-98.

Wall, R.J. "Transgenic Livestock: Progress and Prospects For The Future", *Theriogenology* (1996) 45:57-68.

Houdebine, Louis-Marie, "Production of pharmaceutical proteins from transgenic animals", *J. Biotech* (1994) 34:269-287.

Kappel, Catherine A., et al. "Regulating gene expression in transgenic animals", *Current Opinions in Biotechnology* (1992) 3:548-553.

Cameron, Ewan R., "Recent Advances in Transgenic Technology", *Molecular Biology* (1997) 7:253-265.

Niemann, H. "Transgenic farm animals get off the ground", *Transgenic Research*. (1998) 7:73-75.

Mullins, John H., et al. "Transgenesis in Nonmurine Species", *Hypertension* (1993) 22:630-633.

Mullins, J.J., et al. "Fulminant hypertension in transgenic rats harbouring the mouse *Ren-2* gene", *Nature* (1990) 344:541-544.

Hammer, Robert E., et al. "Spontaneous Inflammatory Disease in Transgenic Rats Expressing HLA-B27 and Human $\beta_2$m: An Animal Model of HLA-B27-Associated Human Disorders", *Cell* (1990) 63:1099-1112.

Mullins, J.J., et al. "Expression of the DBA/2J *Ren-2* gene in the adrenal gland of transgenic mice", *EMBO Journal* (1989) 8(13):4065-4072.

Taurog, Joel D., et al. "HLA-B27 in Inbred and Non-Inbred Transgenic Mice", *Journal of Immunology* (1988) 141(11):4020-4023.

Mullins, Linda J., et al. "Transgenesis in the Rat and Larger Mammals", *J. Clin. Invest*. (1996) 98:S37-S40.

Chaudhary, et al. "A rapid method of cloning functional variable-region antibody genes in *Escherichia coli* as single-chain Immunotoxins", *PNAS* (1990) 87:1066-1070.

Alvarez, R.D., et al. "A phase I study of recombinant adenovirus vector-mediated delivery of an anti-erbB-2 single-chain (sFv) antibody gene for previously treated ovarian and extraovarian cancer patients", *Human Gene Therapy* (1997) 8(2):229-242.

Deshane, Jessy et, al. "Targeted tumor killing via an intracellular antibody against erbB-2", *Journal of Clinical Investigation* (1995) 96(6):2980-2989.

Wels, W., et al. "Biotechnological and gene therapeutic strategies in cancer treatment", *Gene* (1995) 159(1):73-80.

Whittington, H.A., et al. "Recombinant adenoviral delivery for in vivo expression of scFv antibody fusion proteins", *Gene Therapy* (1998) 5:770-777.

Jannot, C.B., et al. "Intracellular Expression of a Single-Chain Antibody Directed to the EGFR Leads to Growth Inhibition of Tumor Cells", *Oncogene* (1996) 13(2):275-282.

Lamikanra, A., et al. "In vivo evaluation of an EIAV vector for the systemic genetic delivery of therapeutic antibodies", *Gene Therapy* (2005) 12(12):988-998.

Arafat, W.O., et al. "Effective single chain antibody (scFv) concentrations in vivo via adenoviral vector mediated expression of secretory scFv", *Gene Therapy* (2002) 9(4):256-262.

Myers, K. A., et al. "Targeting Immune Effector Molecules to Human Tumor Cells Through Genetic Delivery of 5T4-Specific scFv Fusion Proteins", *Cancer Gene Therapy* (2002) 9(11):884-896.

Promega, *Catalog of Nucleic Acids* (1993/94) p. 215-216.

\* cited by examiner

FIG. 1A

SEQ ID No. 1.

```
1   GAGGTCCAGC TTCAGCAGTC TGGACCTGAC CTGGTGAAGC CTGGGGCTTC
     E   V   Q   L   Q   Q   S   G   P   D   L   V   K   P   G   A   S

51  AGTGAAGATA TCCTGCAAGG CTTCTGGTTA CTCATTCACT GGCTACTACA
     V   K   I   S   C   K   A   S   G   Y   S   F   T   G   Y   Y

101 TGCACTGGGT GAAGCAGAGC CATGGAAAGA GCCTTGAGTG GATTGGACGT
     M   H   W   V   K   Q   S   H   G   K   S   L   E   W   I   G   R

151 ATTAATCCTA ACAATGGTGT TACTCTCTAC AACCAGAAAT TCAAGGACAA
     I   N   P   N   N   G   V   T   L   Y   N   Q   K   F   K   D   K

201 GGCCATATTA ACTGTAGACA AGTCATCCAC CACAGCCTAC ATGGAGCTCC
     A   I   L   T   V   D   K   S   S   T   T   A   Y   M   E   L

251 GCAGCCTGAC ATCTGAGGAC TCTGCGGTCT ATTACTGTGC AAGATCTACT
     R   S   L   T   S   E   D   S   A   V   Y   Y   C   A   R   S   T

301 ATGATTACGA ACTATGTTAT GGACTACTGG GGTCAAGTAA CCTCAGTCAC
     M   I   T   N   Y   V   M   D   Y   W   G   Q   V   T   S   V   T

351 CGTCTCCTCA GGTGGTGGTG GGAGCGGTGG TGGCGGCACT GGCGGCGGCG
     V   S   S   G   G   G   G   S   G   G   G   T   G   G   G

401 GATCTAGTAT TGTGATGACC CAGACTCCCA CATTCCTGCT TGTTTCAGCA
     G   S   S   I   V   M   T   Q   T   P   T   F   L   L   V   S   A

451 GGAGACAGGG TTACCATAAC CTGCAAGGCC AGTCAGAGTG TGAGTAATGA
     G   D   R   V   T   I   T   C   K   A   S   Q   S   V   S   N   D

501 TGTAGDTTGG TACCAACAGA AGCCAGGGCA GTCTCCTACA CTGCTCATAT
     V   A   W   Y   Q   Q   K   P   G   Q   S   P   T   L   L   I

551 CCTATACATC CAGTCGCTAC GCTGGAGTCC CTGATCGCTT CATTGGCAGT
     S   Y   T   S   S   R   Y   A   G   V   P   D   R   F   I   G   S

601 GGATATGGGA CGGATTTCAC TTTCACCATC AGCACTTTGC AGGCTGAAGA
     G   Y   G   T   D   F   T   F   T   I   S   T   L   Q   A   E   D

651 CCTGGCAGTT TATTTCTGTC AGCAAGATTA TAATTCTCCT CCGACGTTCG
     L   A   V   Y   F   C   Q   Q   D   Y   N   S   P   P   T   F

701 GTGGAGGCAC CAAGCTGGAA ATCAAACGG
     G   G   G   T   K   L   E   I   K   R
```

FIG. 1B  SEQ ID No. 2.

```
1    AAGCTTCCAC CATGGGATGG AGCTGTATCA TCCTCTTCTT GGTAGCAACA
         A  S  T   M  G  W    S  C  I   I  L  F  L   V  A  T

51   GCTACAGGTG TCCACTCCGA GGTCCAGCTT CAGCAGTCTG GACCTGACCT
      A  T  G   V  H  S  E   V  Q  L   Q  Q  S    G  P  D  L

101  GGTGAAGCCT GGGGCTTCAG TGAAGATATC CTGCAAGGCT TCTGGTTACT
      V  K  P   G  A  S    V  K  I  S   C  K  A   S  G  Y

151  CATTCACTGG CTACTACATG CACTGGGTGA AGCAGAGCCA TGGAAAGAGC
      S  F  T  G   Y  Y  M   H  W  V   K  Q  S  H   G  K  S

201  CTTGAGTGGA TTGGACGTAT TAATCCTAAC AATGGTGTTA CTCTCTACAA
      L  E  W   I  G  R  I   N  P  N   N  G  V    T  L  Y  N

251  CCAGAAATTC AAGGACAAGG CCATATTAAC TGTAGACAAG TCATCCACCA
      Q  K  F   K  D  K    A  I  L  T   V  D  K   S  S  T

301  CAGCCTACAT GGAGCTCCGC AGCCTGACAT CTGAGGACTC TGCGGTCTAT
      T  A  Y  M   E  L  R   S  L  T   S  E  D  S   A  V  Y

351  TACTGTGCAA GATCTACTAT GATTACGAAC TATGTTATGG ACTACTGGGG
      Y  C  A  R   S  T  M   I  T  N   Y  V  M   D  Y  W  G

401  TCAAGTAACC TCAGTCACCG TCTCCTCAGG TGGTGGTGGG AGCGGTGGTG
      Q  V  T   S  V  T    V  S  S   G  G  G    S  G

451  GCGGCACTGG CGGCGGCGGA TCTAGTATTG TGATGACCCA GACTCCCACA
      G  G  T  G   G  G  G   S  S  I   V  M  T  Q   T  P  T

501  TTCCTGCTTG TTTCAGCAGG AGACAGGGTT ACCATAACCT GCAAGGCCAG
      F  L  L   V  S  A  G   D  R  V   T  I  T  C   K  A  S

551  TCAGAGTGTG AGTAATGATG TAGCTTGGTA CCAACAGAAG CCAGGGCAGT
      Q  S  V   S  N  D    V  A  W  Y   Q  Q  K   P  G  Q

601  CTCCTACACT GCTCATATCC TATACATCCA GTCGCTACGC TGGAGTCCCT
      S  P  T  L   L  I  S   Y  T  S   S  R  Y  A   G  V  P

651  GATCGTTCAG GCTGAAGACC TGGCAGTTTA TTTCTGTCAG CAAGATTATA
      D  R  F   I  G  S  G   Y  G  T   D  F  T    F  T  I  S

701  CACTTTGCAG GCTGAAGACC TGGCAGTTTA TTTCTGTCAG CAAGATTATA
      T  L  Q   A  E  D    L  A  V  Y   F  C  Q   Q  D  Y
```

FIG. 1C

```
 751 ATTCTCCTCC GACGTTCGGT GGAGGCACCA AGCTGGAAAT CAAACGGGCC
      N  S  P  P   T  F  G   G  G  T    K  L  E  I   K  R  A

801 TCCACCAAGG GCCCATCGGT CTTCCCCCTG GCACCCTCCT CCAAGAGCAC
      S  T  K   G  P  S  V   F  P  L   A  P  S    S  K  S  T

851 CTCTGGGGGC ACAGCGGCCC TGGGCTGCCT GGTCAAGGAC TACTTCCCCG
      S  G  G   T  A  A    T  G  C  L   V  K  D   Y  F  P

901 AACCGGTGAC GGTGTCGTGG AACTCAGGCG CCCTGACCAG CGGCGTGCAC
      E  P  V  T   V  S  W   N  S  G   A  L  T  S   G  V  H

951 ACCTTCCCGG CTGTCCTACA GTCCTCAGGA CTCTACTCCC TCAGCAGCGT
      T  F  P   A  V  L  Q   S  S  G   L  Y  S    L  S  S  V

1001 GGTGACCGTG CCCTCCAGCA GCTTGGGCAC CCAGACCTAC ATCTGCAACG
      V  T  V   P  S  S    S  L  G  T   Q  T  Y   I  C  N

1051 TGAATCACAA GCCCAGCAAC ACCAAGGTGG ACAAGAAAGT TGAGCCCAAA
      V  N  H  K   P  S  N   T  K  V   D  K  K  V   E  P  K

1101 TCTTGTGACA AAACTCACAC ATGCCCACCG TGCCCAGCAC CTGAACTCCT
      S  C  D   K  T  H  T   C  P  P   C  P  A    P  E  L  L

1151 GGGGGGACCG TCAGTCTTCC TCTTCCCCCC AAAACCCAAG GACACCCTCA
      G  G  P   S  V  F    L  F  P  P   K  P  K   D  T  L

1201 TGATCTCCCG GACCCCTGAG GTCACATGCG TGGTGGTGGA CGTGAGCCAC
      M  I  S  R   T  P  E   V  T  C   V  V  V  D   V  S  H

1251 GAAGACCCTG AGGTCAAGTT CAACTGGTAC GTGGACGGCG TGGAGGTGCA
      E  D  P   E  V  K  F   N  W  Y   V  D  G    V  E  V  H

1301 TAATGCCAAG ACAAAGCCGC GGGAGGAGCA GTACAACAGC ACGTACCGTG
      N  A  K   T  K  P    R  E  E  Q   Y  N  S   T  Y  R

1351 TGGTCAGCGT CCTCACCGTC CTGCACCAGG ACTGGCTGAA TGGCAAGGAG
      V  V  S  V   L  T  V   L  H  Q   D  W  L  N   G  K  E

1401 TACAAGTGCA AGGTCTCCAA CAAAGCCCTC CCAGCCCCCA TCGAGAAAAC
      Y  K  C   K  V  S  N   K  A  L   P  A  P    I  E  K  T

1451 CATCTCCAAA GCCAAAGGGC AGCCCCGAGA ACCACAGGTG TACACCCTGC
      I  S  K   A  K  G    Q  P  R  E   P  Q  V   Y  T  L

1501 CCCCATCCCG GGATGAGCTG ACCAAGAACC AGGTCAGCCT GACCTGCCTG
      P  P  S  R   D  E  L   T  K  N   Q  V  S  L   T  C  L
```

FIG. 1D

```
1551 GTCAAAGGCT TCTATCCCAG CGACATCGCC GTGGAGTGGG AGAGCAATGG
      V  K  G    F  Y  P  S    D  I  A    V  E  W    E  S  N  G

1601 GCAGCCGGAG AACAACTACA AGACCACGCC TCCCGTGCTG GACTCCGACG
      Q  P  E    N  N  Y    K  T  T  P    P  V  L    D  S  D

1651 GCTCCTTCTT CCTCTACAGC AAGCTCACCG TGGACAAGAG CAGGTGGCAG
      G  S  F  F    L  Y  S    K  L  T    V  D  K  S    R  W  Q

1701 CAGGGGAACG TCTTCTCATG CTCCGTGATG CATGAGGCTC TGCACAACCA
      Q  G  N    V  F  S  C    S  V  M    H  E  A    L  H  N  H

1751 CTACACGCAG AAGAGCCTCT CCCTGTCTCC GGGTAAATGA GTGCCACGGC
      Y  T  Q    K  S  L    S  L  S  P    G  K  -    V  R  R

1801 CAAGCTT
      P  S
```

FIG. 2A  SEQ ID No. 3.

```
ATGGGCCACA CACGGAGGCA GGGAACATCA CCATCCAAGT GTCCATACCT   50
 M  G  H    T  R  R    Q  G  T  S   P  S  K    C  P  Y  L

CAATTTCTTT CAGCTCTTGG TGCTGGCTGG TCTTTCTCAC TTCTGTTCAG  100
 N  F  F    Q  L  L    V  L  A  G   L  S  H    F  C  S

GTGTTATCCA CGTGACCAAG GAAGTGAAAG AAGTGGCAAC GCTGTCCTGT  150
 G  V  I  H   V  T  K    E  V  K    E  V  A  T   L  S  C

GGTCACAATG TTTCTGTTGA AGAGCTGGCA CAAACTCGCA TCTACTGGCA  200
 G  H  N    V  S  V  E   E  L  A    Q  T  R    I  Y  W  Q

AAAGGAGAAG AAAATGGTGC TGACTATGAT GTCTGGGGAC ATGAATATAT  250
 K  E  K    K  M  V    L  T  M  M   S  G  D    M  N  I

GGCCCGAGTA CAAGAACCGG ACCATCTTTG ATATCACTAA TAACCTCTCC  300
 W  P  E  Y   K  N  R    T  I  F    D  I  T  N   N  L  S

ATTGTGATCC TGGCTCTGCG CCCATCTGAC GAGGGCACAT ACGAGTGTGT  350
 I  V  I    L  A  L  R   P  S  D    E  G  T    Y  E  C  V

TGTTCTGAAG TATGAAAAAG ACGCTTTCAA GCGGGAACAC CTGGCTGAAG  400
 V  L  K    Y  E  K    D  A  F  K   R  E  H    L  A  E

TGACGTTATC AGTCAAAGCT GACTTCCCTA CACCTAGTAT ATCTGACTTT  450
 V  T  L  S   V  K  A    D  F  P    T  P  S  I   S  D  F

GAAATTCCAA CTTCTAATAT TAGAAGGATA ATTTGCTCAA CCTCTGGAGG  500
 E  I  P    T  S  N  I   R  R  I    I  C  S    T  S  G  G

TTTTCCAGAG CCTCACCTCT CCTGGTTGGA AAATGGAGAA GAATTAAATG  550
 F  P  E    P  H  L    S  W  L  E   N  G  E    E  L  N

CCATCAACAC AACAGTTTCC CAAGATCCTG AAACTGAGCT CTATGCTGTT  600
 A  I  N  T   T  V  S    Q  D  P    E  T  E  L   Y  A  V

AGCAGCAAAC TGGATTTCAA TATGACAACC AACCACAGCT TCATGTGTCT  650
 S  S  K    L  D  F  N   M  T  T    N  H  S    F  M  C  L

CATCAAGTAT GGACATTTAA GAGTGAATCA GACCTTCAAC TGGAATACAA  700
 I  K  Y    G  H  L    R  V  N  Q   T  F  N    W  N  T
```

FIG. 2B

```
CCAAGCAAGA GCATTTTCCT GATGGAGGCG GGGGATCCGA GGTCCAGCTT   750
 T  K  Q  E   H  F  P    D  G  G    G  G  S  E   V  Q  L

CAGCAGTCTG CACCTGACCT GGTGAAGCCT GGGGCTTCAG TGAAGATATC   800
 Q  Q  S    G  P  D  L  V  K  P    G  A  S    V  K  I  S

CTGCAAGGCT TCTGGTTACT CATTCACTGG CTACTACATG CACTGGGTGA   850
 C  K  A    S  G  Y    S  F  T  G  Y  Y  M    H  W  V

AGCAGAGCCA TGGAAAGAGC CTTGAGTGGA TTGGACGTAT TAATCCTAAC   900
 K  Q  S  N  G  K  S   L  E  W    I  G  R  I  N  P  N

AATGGTGTTA CTCTCTACAA CCAGAAATTC AAGGACAAGG CCATATTRAC   950
 N  G  V    T  L  Y  N  Q  K  F    K  D  K    A  I  L  T

TGTAGACAAG TCATCCACCA CAGCCTACAT GGAGCTCCGC AGCCTGACAT  1000
 V  D  K    S  S  T    T  A  Y  M  E  L  R    S  L  T

CTGAGGACTC TGCGGTCTAT TACTGTGCAA GATCTACTAT GATTACGAAC  1050
 S  E  D  S  A  V  Y   Y  C  A    R  S  T  M  I  T  N

TATGTTATGG ACTACTGGGG TCAAGTAACC TCAGTCACCG TCTCCTCAGG  1100
 Y  V  M    D  Y  W  G  Q  V  T    S  V  T    V  S  S  G

TGGTGGTGGG AGCGGTGGTG GCGGCACTGG CGGCGGCGGA TCTAGTATTG  1150
 G  G  G    S  G  G    G  G  T  G  G  G  G    S  S  I

TGATGACCCA GACTCCCACA TTCCTGCTTG TTTCAGCAGG AGACAGGGTT  1200
 V  M  T  Q  T  P  T    F  L  L    V  S  A  G  D  R  V

ACCATAACCT GCAAGGCCAG TCAGAGTGTG AGTAATGATG TAGCTTGGTA  1250
 T  I  T    C  K  A  S  Q  S  V    S  N  D    V  A  W  Y

CCAACAGAAG CCAGGGCAGT CTCCTACACT GCTCATATCC TATACATCCA  1300
 Q  Q  K    P  G  Q    S  P  T  L  L  I  S    Y  T  S

GTCGCTACGC TGGAGTCCCT GATCGCTTCA TTGGCAGTGG ATATGGGACG  1350
 S  R  Y  A  G  V  P    D  R  F    I  G  S  G  Y  G  T

GATTTCACTT TCACCATCAG CACTTTGCAG GCTGAAGACC TGGCAGTTTA  1400
 D  F  T    F  T  I  S  T  L  Q    A  E  D    L  A  V  Y

TTTCTGTCAG CAAGATTATA ATTCTCCTCC GACGTTCGGT GGAGGCACCA  1450
 F  C  Q    Q  D  Y    N  S  P  P   T  F  G   G  G  T

AGCTGGAAAT CAAATAA
 K  L  E  I  K
```

B7-1.5T4.1

B7-1.5T4.2

FIG. 4   SEQ ID No. 4.

Molecule Name-: B7-2 (1-241)          738 bps DNA Linear
Sequence Printed:1-738 (Full)         Date Printed 02 Jun 1997
Description:

```
1    ATGGGACTGA GTAACATTCT CTTTGTGATG GCCTTCCTGC TCTCTGGTGC
       M  G  L   S  N  I  L   F  V  M   A  F  L   L  S  G  A

51   TGCTCCTCTG AAGATTCAAG CTTATTTCAA TGAGACTGCA GACCTGCCAT
       A  P  L   K  I  Q    A  Y  F  N   E  T  A   D  L  P

101  GCCAATTTGC AAACTCTCAA AACCAAAGCC TGAGTGAGCT AGTAGTATTT
       C  Q  F   A  N  S  Q   N  Q  S   L  S  E  L   V  V  F

151  TGGCAGGACC AGGAAAACTT GGTTCTGAAT GAGGTATACT TAGGCAAAGA
       W  Q  D   Q  E  N  L   V  L  N   E  V  Y    L  G  K  E

201  GAAATTTGAC AGTGTTCATT CCAAGTATAT GGGCCGCACA AGTTTTGATT
       K  F  D   S  V  H    S  K  Y  M   G  R  T   S  F  D

251  CGGACAGTTG GACCCTGAGA CTTCACAATC TTCAGATCAA GGACAAGGGC
       S  D  S  W   T  L  R   L  H  N   L  Q  I  K   D  K  G

301  TTGTATCAAT GTATCATCCA TCACAAAAAG CCCACAGGAA TGATTCGCAT
       L  Y  Q   C  I  I  H   H  K  K   P  T  G    M  I  R  I

351  CCACCAGATG AATTCTGAAC TGTCAGTGCT TGCTAACTTC AGTCAACCTG
       H  Q  M   N  S  E    L  S  V  L   A  N  F   S  Q  P

401  AAATAGTACC AATTTCTAAT ATAACAGAAA ATGTGTACAT AAATTTGACC
       E  I  V  P   I  S  N   I  T  E   N  V  Y  I   N  L  T

451  TGCTCATCIA TACACGGTTA CCCAGAACCT AAGAAGATGA GTGTTTTGCT
       C  S  S   I  H  G  Y   P  E  P   K  K  M    S  V  L  L

501  AAGAACCAAG AATTCAACTA TCGAGTATGA TGGTATTATG CAGAAATCTC
       R  T  K   N  S  T    I  E  Y  D   G  I  M   Q  K  S

551  AAGATAATGT CACAGAACTG TACGACGTTT CCATCAGCTT GTCTGTTTCA
       Q  D  N  V   T  E  L   Y  D  V   S  I  S  L   S  V  S

601  TTCCCTGATG TTACGAGCAA TATGACCATC TTCTGTATTC TGGAAACTGA
       F  P  D   V  T  S  N   M  T  I   F  C  I    L  E  T  D

651  CAAGACGCGG CTTTTATCIT CACCTTTCTC TATAGAGCTT GAGGACCCTC
       K  T  R   L  L  S    S  P  F  S   I  E  L   E  D  P

701  AGCCTCCCCC AGACCACATT CCTGGAGGCG GGGGATCC
       Q  P  P  P   D  H  I   P  G  G  G   G  S
```

FIG. 11
anti B7.1
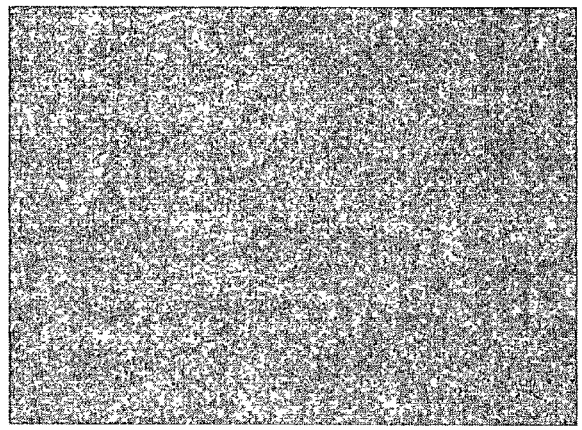
anti c-myc
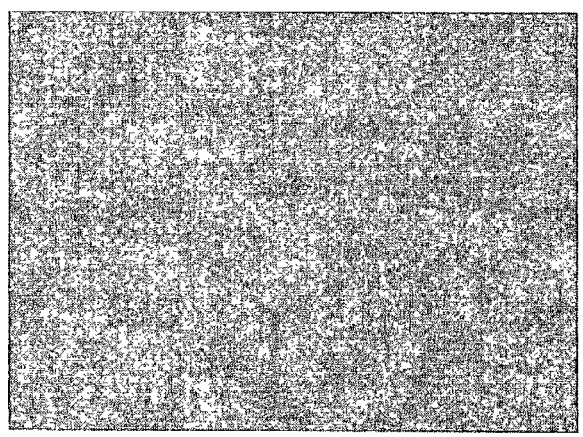
X-gal stain
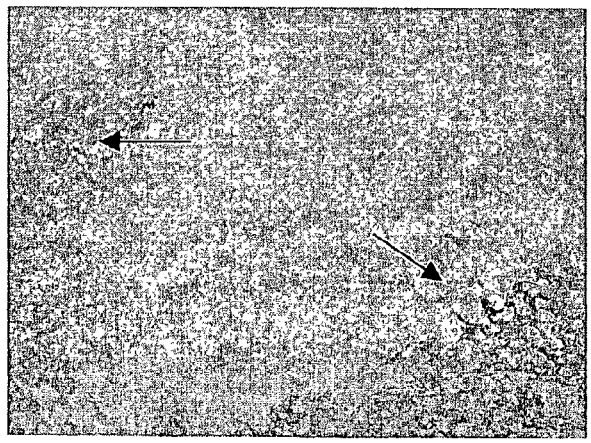

FIG. 12
anti B7.1
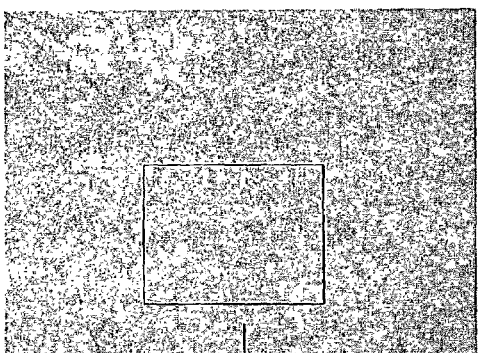
X 100 mag
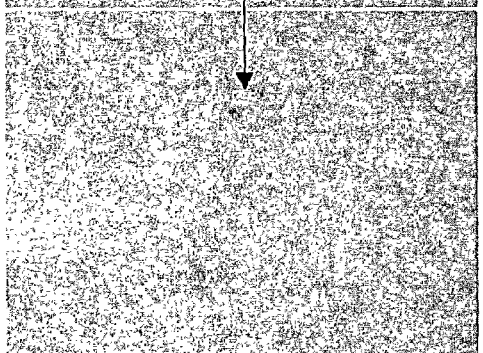
X 200 mag
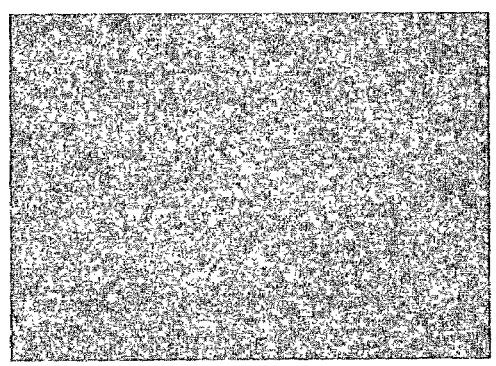
secondary alone
anti c-myc
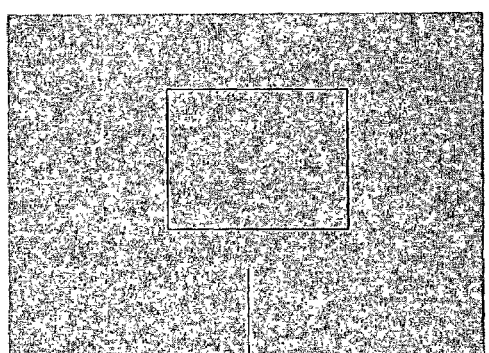
X 100 mag
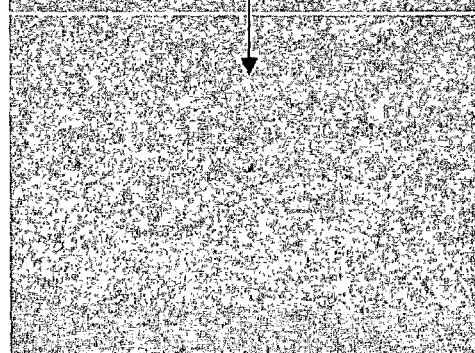
X 200 mag
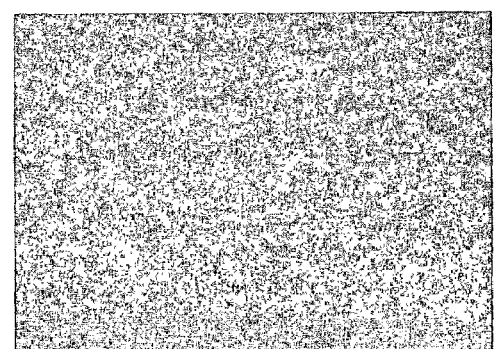
secondary alone

US 7,276,488 B2

VECTOR SYSTEM

CROSS-REFERENCE TO RELATED APPLICATIONS

This application is a Continuation-in-Part application of U.S. patent application Ser. No. 09/445,375 filed 21 Mar. 2000 as the 35 U.S.C. § 371(c) date and is the National Phase of PCT/GB98/01627 filed 4 Jun. 1998, which claims priority under 35 U.S.C. § 119 to Great Britain patent application number 9711579.4 filed 4 Jun. 1997, Great Britain patent application number 9713150.2 filed 20 Jun. 1997 and Great Britain patent application number 9714230.1 filed 4 Jul. 1997, and a Continuation-in-Part application of PCT No. PCT/GB00/04317, designating inter alia the US and published in English, filed 13 Nov. 2000, claiming priority from PCT/GB99/03859 and GB 0003527.9 and GB 0005071.6.

Reference is made in this application to the following applications:

U.S. patent application Ser. No. 09/532,909 filed 22 Mar. 2000 claiming priority from PCT/GB98/02867 and GB 0005846.1

U.S. patent application Ser. No. 09/533,276 filed 22 Mar. 2000 claiming priority from PCT/GB98102867 and GB 0005841.2

U.S. patent application Ser. No. 09/533,295 filed 22 Mar. 2000 claiming priority from PCT/GB98/02867 and GB 0005844.6

PCT No. PCT/GB98/02867 filed 23 Sep. 1998 claiming priority of GB 9720465.5 designating inter alia the US;

PCT No. PCT/GB98/02885 filed 23 Sep. 1998 claiming priority of GB 9720216.2 designating inter alia the US;

U.S. Ser. No. 09/238,356 filed 27 Jan. 1999 claiming priority of GB 9811037.2 and GB 9727135.7;

PCT No. PCT/GB99/00325 filed 17 Feb. 1999 claiming priority of GB 9803351.7 designating inter alia the US;

PCT No. PCT/GB99/00672 filed 5 May 1999 claiming priority of GB 9902081.0, GB 9818103.5 and GB 9804841.6 designating inter alia the US;

PCT No. PCT/GB99/00764 filed 5 May 1999 claiming priority of GB 9902081.0, GB 9818103.5 and GB 9804841.6 designating inter alia the US;

U.S. 60/093,149 filed 17 Jul. 1998 claiming priority of GB 9811152.9;

PCT No. PCT/GB99/03866 filed 19 Nov. 1999 claiming priority of GB 9825524.3 designating inter alia the US;

PCT No. PCT/GB00/00520 filed 15 Feb. 2000 claiming priority of GB 9903408.4 designating inter alia the US; and PCT No. PCT/GB99/03181 filed 22 Sep. 1999 claiming priority of GB 9903538.8, GB 9901906.9 and PCT/GB98/02885 designating inter alia the US.

Each of the aforementioned applications, and each document cited in each of the aforementioned applications—either in the text thereof or during the prosecution thereof—("application cited documents") and each document referenced or cited in each of the application cited documents, is hereby incorporated herein by reference. Likewise, each document cited in this text ("herein cited documents") and each document referenced or cited in herein cited documents, is hereby incorporated herein by reference.

FIELD OF THE INVENTION

The present invention relates to a vector system.

In particular, the present invention relates to a vector system comprising a nucleotide sequence capable of encoding an antibody in vivo.

SUMMARY OF ASPECTS OF THE PRESENT INVENTION

According to a first aspect of the present invention there is provided a vector system comprising a nucleotide sequence ("NS") coding for an antibody.

The vector system may be a non-viral system or a viral vector system.

The vector system may also comprise a nucleotide sequence of interest ("NOI") which optionally encodes a protein of interest ("POI").

According to a second aspect of the present invention there is provided a method of treating and/or preventing a disease in a subject in need of same, the method comprising the step of administering a vector system according to the first aspect of the invention to the subject, such that the NS is expressed in vivo to produce said antibody.

According to a third aspect, the present invention also provides the use of a vector system according to the first aspect of the invention in the manufacture of a medicament to treat and/or prevent a disease in a subject in need of same, wherein the NS is expressed in vivo to produce said antibody.

The disease may be a cancerous or non-cancerous disease.

For cancerous diseases, the present invention also provides a method of delivering a nucleotide sequence of interest ("NOI") and/or a product of interest ("POI") to a tumour, which comprises the step of using a vector system according to the first aspect of the invention wherein the antibody is a tumour-interacting protein ("TIP").

DETAILED DESCRIPTION OF THE INVENTION

Vector System

The present invention relates to a vector system, in particular a vector system comprising a nucleotide sequence coding for an antibody.

As it is well known in the art, a vector is a tool that allows or facilitates the transfer of an entity from one environment to another. By way of example, some vectors used in recombinant DNA techniques allow entities—such as a segment of DNA (such as a heterologous DNA segment, such as a heterologous cDNA segment)—to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Gene therapy includes any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology (Ed Robert Meyers, Pub VCH, such as pages 556-558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favourable phenotype; cells can be manipulated at the molecular level to treat cancer (Schmidt-Wolf and Schmidt-Wolf, 1994, Annals of Hematology 69;273-279) or other conditions—such as immune, cardiovascular, neurological, inflammatory or infectious disorders; antigens can be manipulated and/or introduced to elicit an immune response—such as genetic vaccination.

The vector of the present invention may be a viral vector or a non-viral vector.

In a first preferred embodiment, the vector is a non-viral vector. Non-viral delivery systems include but are not limited to DNA transfection methods. Here transfection includes a process using a non-viral vector to deliver a gene to a target mammalian cell. Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof. Viral delivery systems include but are not limited to adenovirus vector, an adeno-associated viral (MV) vector, a herpes viral vector, retroviral vector, lentiviral vector, baculoviral vector. Other examples of vectors include ex vivo delivery systems—which include but are not limited to DNA transfection methods such as electroporation, DNA biolistics, lipid-mediated transfection, compacted DNA-mediated transfection).

In a second preferred embodiment the vector is a viral vector.

Preferably the vector is a retroviral vector.

In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In slightly more detail, a retrovirus is a virus which contains genomic RNA which on entry into a host cell is converted to a DNA molecule by a reverse transcriptase enzyme. The DNA copy serves as a template for the production of new RNA genomes and virally encoded proteins necessary for the assembly of infectious viral particles. Thus, a retrovirus is an infectious entity that replicates through a DNA intermediate.

There are many retroviruses and examples include: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763).

Details on the genomic structure of some retroviruses may be found in the art. By way of example, details on HIV may be found from the NCBI Genbank (i.e. Genome Accession No. AF033819).

All retroviruses contain three major coding domains, gag, pol, env, which code for essential virion proteins. Nevertheless, retroviruses may be broadly divided into two categories: namely, "simple" and "complex". These categories are distinguishable by the organization of their genomes. Simple retroviruses usually carry only this elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: J M Coffin, S M Hughes, H E Varmus pp 1-25).

All oncogenic members except the human T-cell leukemia virus-bovine leukemia virus group (HTLV-BLV) are simple retroviruses. HTLV, BLV and the lentiviruses and spumaviruses are complex. Some of the best studied oncogenic retroviruses are Rous sarcoma virus (RSV), mouse mammary tumour virus (MMTV) and murine leukemia virus (MLV) and the human T-cell leukemia virus (HTLV).

The vector system of the present invention may be a lentiviral vector system.

The lentivirus group of retroviruses can be split into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11; 3053-3058, Lewis and Emerman 1994 J. Virol. 68: 510-516). In contrast, other retroviruses—such as MLV—are unable to infect non-dividing cells such as those that make up, for example, muscle, brain, lung and liver tissue.

In one embodiment of the present invention, the features of adenoviruses may be combined with the genetic stability of retroviruses/lentiviruses which can be used to transduce target cells to become transient retroviral producer cells capable of stably infect neighbouring cells. Such retroviral producer cells which are engineered to express an antibody can be implanted in organisms such as animals or humans.

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems, such as those described for example in WO 95/30018.

The present invention also provides a hybrid viral vector system for in vivo delivery of a nucleotide sequence encoding an antibody, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on an adenoviral vector and/or the secondary viral vector is obtainable from or is based on a retroviral vector preferably a lentiviral vector.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called "budding".

As already indicated, each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For ease of understanding, a simple, generic diagram (not to scale) of a retroviral genome showing the elementary features of the LTRs, gag, pol and env is presented below.

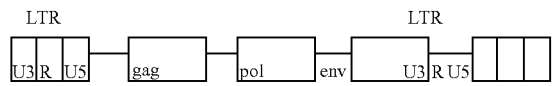

For the viral genome, the site of transcription initiation is at the boundary between U3 and R in the left hand side LTR (as shown above) and the site of poly (A) addition (termination) is at the boundary between R and U5 in the right hand side LTR (as shown above). U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

As shown in the diagram above, the basic molecular organization of a retroviral RNA genome is (5') R—U5—gag, pol, env-U3-R (3'). In a retroviral vector genome gag, pol and env are absent or not functional. The R regions at both ends of the RNA are repeated sequences. U5 and U3 represent sequences unique, respectively, to the 5' and 3' ends of the RNA genome. These three sets of end sequences go to form the long terminal repeats (LTRs) in the proviral DNA, which is the form of the genome which integrates into the genome of the infected cell. The LTRs in a wild type retrovirus consist of (5')U3—R—U5 (3'), and thus U3 and U5 both contain sequences which are important for proviral integration. Other essential sequences required in the genome for proper functioning include a primer binding site for first strand reverse transcription, a primer binding site for second strand reverse transcription and a packaging signal.

With regard to the structural genes gag, pol and env themselves and in slightly more detail, gag encodes the internal structural protein of the virus. Gag is proteolytically processed into the mature proteins MA (matrix), CA (capsid), NC (nucleocapsid). The gene pol encodes the reverse transcriptase (RT), which contains both DNA polymerase, and associated RNase H activities and integrase (IN), which mediates replication of the genome. The gene env encodes the surface (SU) glycoprotein and the transmembrane (TM) protein of the virion, which form a complex that interacts specifically with cellular receptor proteins. This interaction leads ultimately to fusion of the viral membrane with the cell membrane.

The envelope protein is a viral protein which coats the viral particle and plays an essential role in permitting viral entry into a target cell. The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesised in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they do play an essential role in the entry process. In this regard, the SU domain binds to a receptor molecule—often a specific receptor molecule—on the target cell. It is believed that this binding event activates the membrane fusion-inducing potential of the TM protein after which the viral and cell membranes fuse. In some viruses, notably MLV, a cleavage event—resulting in the removal of a short portion of the cytoplasmic tail of TM—is thought to play a key role in uncovering the full fusion activity of the protein (Brody et al 1994 J. Virol. 68: 4620-4627, Rein et al 1994 J. Virol. 68: 1773-1781). This cytoplasmic "tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. Here, transduction includes a process of using a viral vector to deliver a non-viral gene to a target cell. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an envelope protein with an erythropoietin segment produced a recombinant retrovirus which then bound specifically to human cells that expressed the erythropoietin receptor on their surface, such as red blood cell precursors (Maulik and Patel 1997 "Molecular Biotechnology: Therapeutic Applications and Strategies" 1997. Wiley-Liss Inc. pp 45.).

In addition to gag, pol and env, the complex retroviruses also contain "accessory" genes which code for accessory or auxiliary proteins. Accessory or auxiliary proteins are defined as those proteins encoded by the accessory genes in addition to those encoded by the usual replicative or structural genes, gag, pol and env. These accessory proteins are distinct from those involved in the regulation of gene expression, like those encoded by tat, rev, tax and rex. Examples of accessory genes include one or more of vif, vpr, vpx, vpu and nef. These accessory genes can be found in, for example, HIV (see, for example pages 802 and 803 of "Retroviruses" Ed. Coffin et al Pub. CSHL 1997). Non-essential accessory proteins may function in specialized cell types, providing functions that are at least in part duplicative of a function provided by a cellular protein. Typically, the accessory genes are located between pol and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral tat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (other wise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158:1-24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targeted cell or a targeted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to infect cells to introduce the NOI into the genome of the cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449). However, this technique can be problematic in the sense that the titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

More recently, packaging cells have been developed in which the gag, pol and env viral coding regions are carried on separate expression plasmids that are independently transfected into a packaging cell line so that three recombinant events are required for wild type viral production. This strategy is sometimes referred to as the three plasmid transfection method (Soneoka et al 1995 Nucl. Acids Res. 23: 628-633).

Transient transfection can also be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI. Vector production involves transient transfection of one or more of these components into cells containing the other required components. If the vector encodes toxic genes or genes that interfere with the replication of the host cell, is such as inhibitors of the cell cycle or genes that induce apotosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatis virus (VSV). Insertion of the Env protein of VSV facilitates vector concentration as HIV/VSV-G vectors with titres of $5 \times 10^5$ ($10^8$ after concentration) were generated by transient transfection (Naldini et al 1996 Science 272: 263-267). Thus, transient transfection of HIV vectors may provide a useful strategy for the generation of high titre vectors (Yee et al 1994 PNAS. 91: 9564-9568).

If the retroviral component includes an env nucleotide sequence, then all or part of that sequence can be optionally replaced with all or part of another env nucleotide sequence. Replacement of the env gene with a heterologous env gene is an example of a technique or strategy called pseudotyping. Pseudotyping is not a new phenomenon and examples may be found in WO-A-98/05759, WO-A-98/05754, WO-A-97/17457, WO-A-96/09400, WO-A-91/00047 and Mebatsion et al 1997 Cell 90, 841-847.

Pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389:239-242). By way of example—workers have pseudotyped an HIV based vector with the glycoprotein from VSV (Verma and Somia 1997 ibid). Alternatively, env can be modified so as to affect (such as to alter) its specificity.

Thus, the term "recombinant retroviral vector" describes an entity (such as a DNA molecule) which contains sufficient retroviral sequences to allow an RNA transcript of the vector to be packaged in the presence of essential retroviral proteins into a retroviral particle capable of infecting a target cell. Infection of the target cell includes reverse transcription and integration into the target cell genome.

The term "recombinant retroviral vector" also covers a retroviral particle containing an RNA genome encoded by the DNA molecule. The retroviral vector will also contain non-viral genes which are to be delivered by the vector to the target cell. A recombinant retroviral vector is incapable of independent replication to produce infectious retroviral particles. Usually, a recombinant retroviral vector lacks functional gag-pol and/or env genes, or other genes encoding proteins essential for replication.

The term "targeted retroviral vector" means a recombinant retroviral vector whose ability to infect a cell or to be expressed in the target cell is restricted to certain cell types within the host organism. An example of targeted retroviral vectors is one with a genetically modified envelope protein which binds to cell surface molecules found only on a limited number of cell types in the host organism. Another example of a targeted retroviral vector is one which contains promoter and/or enhancer elements which permit expression of one or more retroviral transcripts in only a proportion of the cell types of the host organism.

NS/NOI

The vector system of the present invention comprises a nucleotide sequence ("NS") coding for an antibody. The system may also comprise a nucleotide of Interest ("NOI") which may optionally encode a protein of interest ("POI")

On occasions in the following text, the NS and NOI may be individually or collectively referred to as being a gene.

The NS and NOI can be any suitable nucleotide sequence. For example, the NOI can be, for example, a synthetic DNA or RNA sequence, a natural DNA or RNA sequence, a recombinant DNA or RNA sequence (i.e. prepared by use of recombinant DNA techniques), a cDNA sequence or a partial genomic DNA sequence, including combinations thereof. The NOI may be a sense sequence or an antisense sequence.

There may be a plurality of NSs or NOIs, which may be directly or indirectly joined to each other, or combinations thereof. Thus, the expressed product may have two or more effector domains (which may be the same or different) and/or two or more "antibody" domains (which may be the same or different).

The NS encodes an antibody (see below).

The NOI may encode a protein of interest ("POI"). In this way, the vector system could be used to examine the effect of expression of a foreign gene on the target cells (such as a tumour cell). By way of example, the vector system could be used to screen a cDNA library for a particular effect on specific tumour cells. Alternatively the POI may have therapeutic, diagnostic, selection, and/or marker properties (see below).

The POIs may be proteins which are secreted from the cell. Alternatively the NOI expression products may not be secreted and may be active within the cell. For some applications, it is preferred for the NOI expression product to demonstrate a bystander effect or a distant bystander effect; that is the production of the expression product in one cell leading to the modulation of additional, related cells, either neighbouring or distant (e.g. metastatic), which possess a common phenotype.

The NOI may be capable of blocking or inhibiting the expression of a gene in the target cell. For example, the NOI may be an antisense sequence. The inhibition of gene expression using antisense technology is well known in the art.

The NOIs or a sequence derived from the NOIs may be capable of "knocking out" the expression of a particular gene in the target cell (for example, a tumour cell). There are several "knock out" strategies known in the art. For example, the NOI may be capable of integrating in the genome of the target cell so as to disrupt expression of the particular gene. The NOI may disrupt expression by, for example, introducing a premature stop codon, by rendering the downstream coding sequence out of frame, or by affecting the capacity of the encoded protein to fold (thereby affecting its function).

Included in the scope of the invention are oligonucleotide sequences, anti-sense RNA and DNA molecules and ribozymes, which function to destabilise the mRNA or inhibit translation of gene of interest. Such nucleotide sequences may be used in conditions where it would be preferable to decrease gene of interest's nucleotide and protein levels, such as in breast cancer (BRACA genes), Burkift's Lymphoma (c-myc), colon cancer (tumour suppressor deleted in colon cancer (DCC)) (Huerta et al., 2001, *Dig Dis Sci*, 46, 1884-91) and others.

The vector system of the present invention could be used to flood target cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication or integration elements are integrated into the NOI (such as lentivirus derived LTR sequences and Adeno Associated Virus IR sequences.

Modifications of gene expression can be obtained by designing anti-sense sequences to the control regions of, for example, tumour specific target genes, such as the promoters, enhancers, and introns.

Oligonucleotides derived from the transcription initiation site, e.g., between −10 and +10 regions of the leader sequence, are preferred. Anti-sense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Alternatively, the NOI may be capable of enhancing or inducing ectopic expression of a gene in a target cell. The NOI or a sequence derived therefrom may be capable of "knocking in" the expression of a particular gene.

Transfected target cells which express a particular gene, or which lack the expression of a particular gene have applications in drug discovery and target validation. The expression system could be used to determine which genes have a desirable effect on target tumour cells, such as those genes or proteins which are able to trigger apoptosis in the cells. Equally, if the inhibition or blocking of expression of a particular gene is found to have a cytotoxic effect on the target tumour cell, this may open up possible therapeutic strategies which ensure that expression of the gene is not lost.

An NOI delivered by the vector system may be used for selection or marker purposes. For example, the NOI may encode for a selection gene, or a marker gene. Many different selectable markers are known in the art and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenolic acid, xanthine and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow chemical selection of most cells expressing these genes.

The NOI delivered by the vector system may be a therapeutic gene—in the sense that the gene itself may be capable of eliciting a therapeutic effect or it may code for a product that is capable of eliciting a therapeutic effect. In a highly preferred aspect of the present invention, the NOI encodes for an anti-tumour agent.

The NOI may be or encode a palliative agent, i.e. a compound which may provides relief, but not a cure.

In one preferred embodiment, the NOI is capable of encoding a cytotoxic molecule. In particular, the NOI(s) may encode molecules which enhance target cells to perish or which stimulate re-generation and functional recovery in the damaged tissue. In another preferred embodiment, the NOI is capable of encoding an enzyme or enzymes responsible for converting a pro-drug into its active metabolite.

In accordance with the present invention, suitable NOIs include those that are (or can produce entities) of therapeutic and/or diagnostic application such as, but not limited to: cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group).

The term "enzyme" as used herein means a reaction catalysing substance modulating but not limited to protein or polypeptide or a fragment of such protein or polypeptide.

The NOI may also be or encode an antiapoptotic factor or a neuroprotective molecule. The survival of cells during programmed cell death depends critically on their ability to access "trophic" molecular signals derived primarily from interactions with other cells. For example, the NOI may encode a pro-apoptotic gene such as p53 or it may be a gene involved in control of the cell death cascade (such as Bcl-2).

The NOI may be a ribozyme. Ribozymes are enzymatic RNA molecules capable of catalysing the specific cleavage of RNA.

Suitable NOIs for use in the treatment or prevention of ischaemic heart disease include NOIs encoding plasminogen activators. Suitable NOIs for the treatment or prevention of rheumatoid arthritis or cerebral malaria include genes encoding anti-inflammatory proteins, antibodies directed against tumour necrosis factor (TNF) alpha, and anti-adhesion molecules (such as antibody molecules or receptors specific for adhesion molecules).

Examples of hypoxia regulatable therapeutic NOIs can be found in PCT/GB95/00322 (WO-A-9521927).

In addition to the therapeutic gene or genes and the expression regulatory elements described, the delivery system may contain additional genetic elements for the efficient or regulated expression of the gene or genes, including promoters/enhancers, translation initiation signals, internal ribosome entry sites (IRES), splicing and polyadenylation signals.

The NOI or NOIs may be under the expression control of an expression regulatory element, usually a promoter or a promoter and enhancer. The enhancer and/or promoter may be preferentially active in a hypoxic or ischaemic or low glucose environment, such that the NOI is preferentially expressed in the particular tissues of interest, such as in the environment of a tumour, arthritic joint or other sites of ischaemia. Thus any significant biological effect or deleterious effect of the NOI on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof.

Further examples include respiratory airway epithelial cells, hepatocytes, muscle cells, cardiac myocytes, synoviocytes, primary mammary epithelial cells and post-mitotically terminally differentiated non-replicating cells such as macrophages and neurons.

The term "promoter" is used in the normal sense of the art, e.g. an RNA polymerase binding site in the Jacob-Monod theory of gene expression.

The term "enhancer" includes a DNA sequence which binds to other protein components of the transcription initiation complex and thus facilitates the initiation of transcription directed by its associated promoter.

The promoter and enhancer of the transcription units encoding the secondary delivery system are preferably strongly active, or capable of being strongly induced, in the primary target cells under conditions for production of the secondary delivery system. The promoter and/or enhancer may be constitutively efficient, or may be tissue or temporally restricted in their activity. Examples of temporally restricted promoters/enhancers are those which are responsive to ischaemia and/or hypoxia, such as hypoxia response elements or the promoter/enhancer of a grp78 or a grp94 gene. One preferred promoter-enhancer combination is a human cytomegalovirus (hCMV) major immediate early (MIE) promoter/enhancer combination.

Preferably the promoters of the present invention are tissue specific. That is, they are capable of driving transcription of a NOI or NOI(s) in one tissue while remaining largely "silent" in other tissue types.

The term "tissue specific" means a promoter which is not restricted in activity to a single tissue type but which nevertheless shows selectivity in that they may be active in one group of tissues and less active or silent in another group.

The level of expression of an NOI or NOIs under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity.

A number of tissue specific promoters, described above, may be particularly advantageous in practising the present invention. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Promoters suitable for cardiac-specific expression include the promoter from the murine cardiac α-myosin heavy chain (MHC) gene. Suitable vascular endothelium-specific promoters include the Et-1 promoter and von Willebrand factor promoter.

Prostate specific promoters include the 5'flanking region of the human glandular kallikrein-1 (hKLK2) gene and the prostate specific antigen (hKLK3).

Examples of promoters/enhancers which are cell specific include a macrophage-specific promoter or enhancer, such as CSF-1 promoter-enhancer, or elements from a mannose receptor gene promoter-enhancer (Rouleux et al 1994 Exp Cell Res 214:113-119). Alternatively, promoter or enhancer elements which are preferentially active in neutrophils, or a lymphocyte-specific enhancer such as an IL-2 gene enhancer, may be used.

The vector system of the present invention may delivery the NS and/or NOI to a target cell. The target cell may be any host cell capable of expressing the antibody in vivo (or ex vivo). The target cell may also be capable of expressing the POI, or the NOi may be delivered to another cell for POI expression.

Where the antibody and/or NOI and/or POI exerts an effect (such as a therapeutic effect) this may be on the target cell. Alternatively the antibody and/or NOI and/or POI may exerts an effect on a different cell. The target cell may act as an in situ factory for production of the antibody and/or NOI and/or POI.

The target cell may be a tumour cell.

The target cell may be a precursor cell such as a haematopoietic (preferably myeloid haematopoietic) cell of the monocyte-macrophage lineage or a precursor of such cells such as a CD34-positive stem cell.

Antibody

The vector system of the present invention comprises a NS encoding an antibody.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

The term "mimetic relates to any chemical which may be a peptide, polypeptide, antibody or other organic chemical which has the same binding specificity as the antibody.

The term "derivative" as used herein includes chemical modification of an antibody. Illustrative of such modifications would be replacement of hydrogen by an alkyl, acyl, or amino group.

A whole immunoglobulin molecule is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portion of the heavy and light chains. Each antibody domain consists of seven antiparallel β-sheets forming a β-barrel with loops connecting the β-strands. Among the loops are the CDR regions. It is feasible to more the CDRs and their associated specificity from one scaffolding β-barrel to another. This is called CDR-grafting. CDR-grafted antibodies appear in early clinical studies not to be as strongly immunogenic as either mouse or chimaeric antibodies. Moreover, mutations may be made outside the CDR in order to increase the binding activity thereof, as in so-called humanised antibodies.

Fab, Fv, and single chain Fv (ScFv) fragments with VH and VL joined by a polypeptide linker exhibit specificities and affinities for antigen similar to the original monoclonal antibodies. The ScFv fusion proteins can be produced with a non-antibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

A large number of monoclonal antibodies and immunoglobulin-like molecules are known which bind specifically to antigens present on the surfaces of particular cell types. Procedures for identifying, characterising, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The antibody used in the present invention may be derived from a human antibody or an engineered, humanised rodent antibody such as a CDR-grafted antibody or may be derived from a phage-display library.

The antigen-binding domain may be comprised of the heavy and light chains of an immunoglobulin, expressed from separate genes, or may use the light chain of an immunoglobulin and a truncated heavy chain to form a Fab or a F(ab)'$_2$ fragment. Alternatively, truncated forms of both heavy and light chains may be used which assemble to form a Fv fragment. An engineered scFv fragment may also be used, in which case, only a single gene is required to encode the antigen-binding domain.

As is well known, antibodies play a key role in the immune system. In brief, the immune system works in three fundamentally different ways: by humoral immunity, by cellular immunity and by secretion of stimulatory proteins, called lymphokines. Humoral immunity relies on proteins collectively called immunoglobulin which constitute about 20% of the proteins in the blood. A singly immunoglobulin molecule is called an antibody but "antibody" is also used to mean many different molecules all directed against the same target molecule. Humoral immunity also involves complement, a set of proteins that are activated to kill bacteria both nonspecifically and in conjunction with antibody.

In cellular immunity, intact cells are responsible for recognition and elimination reactions. The body's first line of defense is the recognition and killing of microorganisms by phagocytes, cells specialized for the ingestion and digestion of unwanted material. These cells include neutrophils and macrophages. A key role of antibodies is to help phagocytes recognise and destroy foreign materials.

In order to perform these functions, the antibody is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Monoclonal antibodies are homogenous antibodies of the same antigenic specificity representing the product of a single clone of antibody-producing cells. It was recognized that monoclonal antibodies offered the basis for human therapeutic products. However, although mouse antibodies are similar to human antibodies, they are sufficiently different that they are recognized by the immune system as foreign bodies, thereby giving rise to an immunological response.

This human-anti-mouse-antibody (HAMA) response limits the usefulness of mouse antibodies as human therapeutic products.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portion of the heavy and light chains. Each antibody domain consists of seven antiparallel β-sheets forming a β-barrel with loops connecting the β-strands. Among the loops are the CDR regions. It is feasible to more the CDRs and their associated specificity from one scaffolding β-barrel to another. This is called CDR-grafting. CDR-grafted antibodies appear in early clinical studies not to be as strongly immunogenic as either mouse or chimaeric antibodies. Moreover, mutations may be made outside the CDR in order to increase the binding activity thereof, as in so-called humanised antibodies.

Fab, Fv, and single chain Fv (ScFv) fragments with VH and VL joined by a polypeptide linker exhibit specificities and affinities for antigen similar to the original monoclonal antibodies. The ScFv fusion proteins can be produced with a nonantibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

In virally directed enzyme therapy (VDEPT), a foreign gene is delivered to normal and cancerous cells by a viral vector—such as a retroviral vector. The foreign gene codes for an enzyme that can convert a non-toxic prodrug (eg 5-fluorocytosine) to a toxic metabolite (5-fluorouracil) that will kill those cells making it (Sikora et al 1994 Ann New York Acad Sci 71b: 115-124). If the promoter utilised is tumour specific, then the toxic product will only be synthesised in the tumour cells. Studies in animal models have demonstrated that this type of treatment can deliver up to 50-fold more drug than by conventional means (Connors and Knox 1995 Stem Cells 13: 501-511). A variation of this technique uses tumour associated antibodies conjugated to prodrug converting enzymes to provide specific delivery to tumours. This method is referred to as antibody-directed enzyme prodrug therapy (ADEPT) (Maulik S and Patel SD "Molecular Biotechnology" 1997 Wiley-Liss Inc pp 45).

A large number of monoclonal antibodies and immunoglobulin-like molecules are known which bind specifically to antigens present on the surfaces of particular cell types such as tumour cells. Procedures for identifying, characterising, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The immunoglobulin or immunoglobulin-like molecule may be derived from a human antibody or an engineered, humanised rodent antibody such as a CDR-grafted antibody or may be derived from a phage-display library or may be a synthetic immunoglobulin-like molecule.

The antigen-binding domain may be comprised of the heavy and light chains of an immunoglobulin, expressed from separate genes, or may use the light chain of an immunoglobulin and a truncated heavy chain to form a Fab or a F(ab)'$_2$ fragment. Alternatively, truncated forms of both heavy and light chains may be used which assemble to form a Fv fragment. An engineered scFv fragment may also be used, in which case, only a single gene is required to encode the antigen-binding domain. In one preferred aspect, the antigen-binding domain is formed from a Fv or a scFv.

When a pathogen invades the body, lymphocytes respond with three types of reaction. The lymphocytes of the humoral system (B cells) secrete antibodies that can bind to the pathogen, signalling its degradation by macrophages and other cells. The lymphocytes of the cellular system (T cells) carry out two major types of functions. Cytotoxic T lymphocytes (CTLs) develop the ability to directly recognise and kill the cells infected by the pathogen. Helper T cells (TH cells) independently recognise the pathogen and secrete protein factors (lymphokines) that stimulate growth and responsiveness of B cells, T cells, and macrophages, thus greatly strengthening the power of the immune response.

In a preferred embodiment, the antibody comprises IgG and/or IgE, or a part thereof, or a bioisostere thereof.

In a more preferred embodiment, the antibody comprises IgG, or a part thereof, or a bioisostere thereof.

5T4

Preferably the antibody recognizes a trophoblast cell surface antigen.

Preferably the antibody recognizes the 5T4 antigen.

The trophoblast cell surface antigen, originally defined by monoclonal antibody 5T4 (Hole and Stern 1988 Br. J. Cancer 57; 239-246), is expressed at high levels on the cells of a wide variety of human carcinomas (Myers et al. 1994 J. Biol. Chem. 269; 9319-9324) but, in normal tissues of non-pregnant individuals, is essentially restricted to low level expression on a few specialized epithelia (Myers et al. ibid. and references therein). The 5T4 antigen has been implicated in contributing to the development of metastatic potential and therefore antibodies specifically recognizing this molecule may have clinical relevance in the treatment of tumours expressing the antigen.

The variable region of the 5T4 monoclonal antibody can also be humanised by a number of techniques, which are known in the art, including grafting of the CDR region sequences on to a human backbone. These can then be used to construct an intact humanised antibody or a humanised single chain antibody (Sab), such as an ScFv coupled to an Fc region (see Antibody Engineering: a practical approach, ed McCafferty et al. 1996 OUP).

Here the term Sab is not limited to just a human or a humanised single chain antibody. Preferably, however the Sab is a human single chain antibody or a humanised single chain antibody, or part thereof—such as ScFv coupled to an Fc region.

In accordance with the invention, standard molecular biology techniques may be used which are within the level of skill in the art. Such techniques are fully described in the literature. See for example; Sambrook et al. (1989) Molecular Cloning; a laboratory manual; Hames and Glover (1985-1997) DNA Cloning: a practical approach, Volumes I-IV (second edition). Methods for the engineering of immunoglobulin genes in particular are given in McCafferty et al (1996) Antibody engineering: a practical approach.

Diseases

The delivery of one or more one or more therapeutic genes by a delivery system according to the present invention may be used alone or in combination with other treatments or components of the treatment.

For example, the delivery system of the present invention may be used to deliver one or more NOI(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimers disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the delivery system of the present invention may be used to deliver one or more NOI(s) useful in the treatment of disorders listed in WO-A-98107859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the delivery system of the present invention may be used to deliver one or more NOI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. Leukemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The subject treated by the method of the present invention may be a human or animal subject. Preferably the subject is a mammalian subject, more preferably a human subject.

In one embodiment of the present invention, the disease to be treated is not cancer.

In another embodiment of the present invention, the disease to be treated is not a virally caused disease.

Tumours

In another embodiment, the disease is a cancer.

Preferably the antibody recognizes a tumour. The antibody may be a tumour interacting protein, i.e. specific for a tumour. The antibody may be able to bind specifically to a tumour, and be a tumour binding protein (TBP). Preferably the antibody is capable of interacting specifcally with at least one tumour associated cell surface molecule.

The vector system may also comprise an NOI, optionally encoding a POI. In use the vector system may be capable of delivering the NOI and/or the POI to the interior of a tumour mass.

In addition to cancerous cell, the cell types present within a tumour mass include but are not limited to macrophages, lymphocytes, tumour infiltrating lymphocyes, endothelial cells etc.

The POI may also comprise at least one tumour binding domain capable of interacting with at least one tumour associated cell surface molecule ("TACSM").

In accordance with the present invention the TACSM can include but is not limited to a cell surface molecule which plays a role in tumour cell growth, migration or metastasis, a receptor for adhesive proteins such as the integrin vitronectin receptor, a growth factor receptor (such as epidermal growth factor (EGF) receptor, platelet-derived growth factor (PDGF) receptor, fibroblast-derived growth factor (FDGF) receptor, nerve growth factor receptor, insulin-like growth factor (IGF-1) receptor; a plasminogen activator; a metalloproteinase (such as collagenase) 5T4 antigen; a tumour specific carbohydrate moiety; an oncofetal antigen; a mucin; a growth factor receptor; a glycoprotein; and an antigen restricted in its tissue distribution.

Preferably the TACSM is selectively expressed on one cell type or on a restrictive number of cell types.

Preferably in use the vector system is capable of delivering an NOI and/or POI to a selective tumour site.

Examples of a TBP include: an adhesion molecule such as Intercellular adhesion molecule, ICAM-1, ICAM-2, LFA-1, LFA-2, LFA-3, LECAM-1, VLA-4, ELAM, N-CAM, N-cadherin, P-Selectin, CD44 and its variant isoforms (in particular CD44v6, CD44v7-8), CD56; a growth factor receptor ligand such epidermal growth factor (EGF), Platelet-derived growth factor (PDGF), Fibroblast-derived growth factor (FDGF), Nerve growth factor, vasopressin, insulin, insulin-like growth factor (IGF-1), hepatocyte growth factor, nerve growth factor, human growth factor, brain derived growth factor, ciliary neutrophic factor, glial cell line-derived growth factor; heavy and light chain sequences from an immunoglobulin (Ig) variable region (from human and animal sources), engineered antibody or one from a phage display library. A phage display library is a technique of expressing immunoglobulin genes in bacteriophage has been developed as a means for obtaining antibodies with the desired binding specificities. Expression systems, based on bacteriophage lambda, and more recently filamentous phage have been developed. The bacteriophage expression systems can be designed to allow heavy and light chains to form random combinations which are tested for their ability to bind the desired antigen.

The TBP may contain an effector domain which is activated on binding of the TPB to the TASCM. The effector domain or domains may be activated on binding of the TBP to a TASCM leading to inhibition of tumour cell proliferation, survival or dissemination. The effector domain may possess enzymatic activity (such as a pro-drug activating enzyme) or the effector domain may include a toxin, or an immune enhancer, such as a cytokine/lymphokine such as those listed above.

Preferably the TBP comprises one or more binding domains capable of interacting with one or more TACSMs which are present on the cancerous cells—which TACSMs may be the same or different.

The term "interacting" includes direct binding, leading to a biological effect as a result of such binding.

Preferably the vector system is used to deliver the antibody and/or an NOI and/or POI ex vivo and/or in vivo to a tumour.

The vector system of the present invention is useful in gene therapy for delivering the antibody and/or an NOI and/or POI to a selective site.

In a preferred aspect, the present invention relates to the delivery of TBP-encoding genes to the site of a tumour. This has considerable advantages for medical applications (such as therapeutic applications) in which TBPs are indicated since it circumvents a number of problems associated with delivery of proteins systemically in humans.

In contrast to the problems associated with production and delivery of proteins, the methods of the invention allow the delivery of genes to the site of the tumour, thus circumventing a number of production problems. The TBPs are thereby produced in situ in the autologous human cells, which serve as a local factory for the production of the gene-based medicament (such as a therapeutic). This has significant advantages in minimising systemic toxicity. The activity of the protein is maximal since the glycosylation of the protein shows a human pattern appropriate to the individual being treated.

The methods of the invention can be used in conjunction with direct injection into the site of the tumour or systemic delivery of, for example targeted vectors or engineered haematopoietic (preferably myeloid haematopoietic) cells or their progenitors. Systemic delivery may be particularly advantageous in a number of indications, particularly in the treatment of disseminated disease. In these cases the gene delivery system or engineered cells can be administered intravenously by bolus injection or by infusion in a suitable formulation. A pharmaceutically acceptable formulation may include an isotonic saline solution, a buffered saline solution or a tissue-culture medium. Additional formulatory agents may be included such as preservative or stabilising agents.

Costimulatory Molecules

Lymphocytes require at least two distinct signals in order to respond to antigens by activation of effector functions (Bretscher and Cohn 1970 Science 169: 1042-1049; Crabtree 1989 Science 243: 355-361). The primary signal is specific for antigen. For B-lymphocytes, the B-cell antigen receptor (surface immunoglobulin) recognizes three-dimensional epitopes on a variety of macromolecules. For T-lymphocytes, the T-cell receptor (TCR) recognizes peptide antigens displayed on the surface of antigen-presenting cells by proteins of the major histocompatability (MHC) family (Weiss et al; 1986 Ann. Rev. Immunol. 4: 593-619).

Stimulation of the primary signal in isolation normally leads to apoptosis (programmed cell death) of the lymphocyte or leads to the establishment of a state of sustained unresponsiveness or anergy (Weiss et al. supra). In order to achieve activation of the lymphocyte, accessory signals are required which may be delivered by cytokines or by cell-surface co-stimulatory ligands present on antigen-presenting cells (APC).

There are a number of such co-stimulatory molecules now identified including adhesion molecules, LFA-3, ICAM-1, ICAM-2. Major co-stimulatory molecules present on APC are the members of the B7 family including B7-1 (CD80), B7-2 (CD86) and B7-3. These molecules are ligands of co-stimulatory receptors on lymphocytes including CD28 (WO092/00092), probably the most significant co-stimulatory receptor for resting T-cells. Different members of the B7 family of glycoproteins may deliver subtly different signals to T-cells (Nunes et al. 1996 J. Biol. Chem. 271: 1591-1598).

Established tumours, despite the fact that they commonly express unusual antigens on their surfaces, are poorly immunogenic. It has been postulated previously that one method for stimulating immune recognition of tumour cells would be to enhance antigen presentation and co-stimulation of lymphocytes in the context of tumour antigens. Transfection of the genes encoding B7-1 and B7-2, alone or in combination with cytokines, have been shown to enhance the development of immunity to experimental tumours in animal models (e.g. Leong et al. 1997 Int. J. Cancer 71: 476482; Zitvogel et al 1996 Eur. J. Immunol. 26:1335-1341; Cayeux et al. 1997 J. Immunol 158:2834-2841). However, in translating these results into a practical treatment for human cancer, there are a number of significant problems to be overcome. A major problem in such studies is the need to deliver B7 genes in vivo to a large number of cells of the tumour to achieve efficacy. A second problem is that it is important to target expression of B7 to the tumour cells to avoid inappropriate immune cell activation directed against other cell types.

This aspect of the present invention solves these specific problems by delivering a gene encoding a secreted co-stimulatory molecule ("SCM") with binding affinity for a tumour antigen. In this way, a relatively small number of transfected cells within the tumour act as a local factory to produce the co-stimulatory molecule which is shed from the producer cell and binds to other cells in the tumour. The aspect of the present invention has the additional advantage that tumour cells need not be the target for transfection.

The SCM of the invention is a novel engineered fusion protein comprising a signal peptide for secretion from mammalian cells, at least one antigen-binding domain from an immunoglobulin or an immunoglobulin-like molecule and at least one further domain which acts as a co-stimulatory signal to a cell of the immune system. The use of combinations of SCMs containing different co-stimulatory domains is also envisaged. The SCMs are produced by expression of SCM-encoding genes in the autologous cells of the individual to be treated and hence any post-translational modifications added to the protein by the host cell are authentic and provide fully functional protein and appropriate pharmacokinetics.

WO-A-92/00092 describes truncated forms of B7-1, derived by placing a translation stop codon before the transmembrane domain, secreted from mammalian cells. In that particular case, a heterologous signal peptide from the Oncostatin M gene was used. WO-A92/00092 also describes fusion proteins which contain the extracellular domain of B7-1 fused to the Fc region of an immunoglobulin. Such molecules can bind to CD28 on T-cells and serve to stimulate T-cell proliferation. However such stimulation occurs only to a moderate extent unless the B7 or B7-derivative is immobilised on a solid surface.

Gerstmayer et al. (1997 J. 1 mmol. 158: 45844590) describes a fusion of B7-2 to an scFv specific for ErbB2 followed by a myc epitope tag and polyhistidine tag which is secreted when expressed in the yeast *Pichia pastoris*. This molecule retained binding for antigen and co-stimulated proliferation of T-cells prestimulated with PMA and IL-2. However, glycosylation of such a molecule is of the yeast type, which is likely to lead to inappropriate pharmacokinetics in humans.

Thus in a preferred embodiment, the NOI encodes a co-stimulatory molecule or domain thereof. The co-stimulatory molecule or domain thereof may have binding affinity for a tumour antigen. The NS and the NOI may be linked and/or the antibody and POI (which, in this embodiment, comprises a co-stimulatory molecule or domain thereof) may be linked.

In accordance with the present invention, any suitable co-stimulalatory domain(s) may be used. By way of example, co-stimulatory domains can be chosen from extracellular portions of the B7 family of cell-surface glycoproteins, including B7-1, B7-2 and B7-3 or other co-stimulatory cell surface glycoproteins such as but not limited to co-stimulatory receptor-ligand molecules including CD2/LFA-3, LFA-1/ICAM-1 and ICAM-3. Studies have demonstrated that T cell co-stimulation by monocytes is dependent on each of two receptor ligand pathways CD2/LFA-3 and LFA-1/ICAM-1 (Van Seventer et al 1991 Eur J Immunol 21: 1711-1718). In addition, it has been shown that ICAM-3, the third LFA-1 counterreceptor, is a co-stimulatory molecule for resting and activated T lymphocytes (Hernandez-Caselles et al 1993 Eur J Immunol 23: 2799-2806).

Other possible co-stimulatory molecules may include a novel glycoprotein receptor designated SLAM, has been identified which, when engaged, potentiates T-cell expansion in a CD28-independent manner and induces a Th0/Th1 cytokine production profile (Cocks et al 1995 Nature 376: 260-263).

CD6, a cell surface glycoprotein, has also been shown to function as a co-stimulatory and adhesion receptor on T cells. Four CD6 isoforms (CD6a, b, c, d) have been described (Kobarg et al 1997 Eur J Immunol 27: 2971-2980). A role for the very late antigen (VLA-4) integrin in the activation of human memory B cells has also been suggested (Silvy et al 1997 Eur J Immunol 27: 2757-2764). Endothelial cells also provide unique co-stimulatory signals that affect the phenotype of activated CD4+ T cells (Karmann et al 1996 Eur J Immunol 26: 610-617). A B3 protein, present on the surface of lipopolysaccharide-activated B cells, which can provide co-stimulation to resting T cells leading to a predominant release of interleukin (IL)-4 and IL-5 and negligible amounts of IL-2 and interferon gamma has been described (Vinay et al 1995 J Biol Chem 270: 23429-23436). The co-expression of a novel co-stimulatory T cell antigen (A6H) on T cells and tumour cells has suggested a possible function related to common properties of these cells (Labuda et al 1995 Int Immunol 7: 1425-1432).

In one preferred embodiment of the invention, the co-stimulatory domain is a portion of B7-1 or B7-2, more preferably the complete extracellular portion of B7-1 or B7-2.

The SCM is formed by expression of a novel gene encoding a fusion protein containing the antigen-binding domain or domains and the co-stimulatory domain or domains. If the antigen-binding domain is comprised of a heavy and a light chain, the co-stimulatory domain is fused to one or other of the immunoglobulin chains, preferably to the heavy chain. If the antigen-binding domain is a scFv, the co-stimulatory domain is fused to the scFv. The domains can be placed in the order (N-terminus to C-terminus): antigen-binding domain followed by co-stimulatory domain; or co-stimulatory domain followed by antigen-binding domain. Preferably, the co-stimulatory domain is placed at the N-terminus followed by the antigen-binding domain. A signal peptide is included at the N-terminus, and may be for example the natural signal peptide of the co-stimulatory extracellular domain. The different domains may be separated by additional sequences, which may result from the inclusion of convenient restriction-enzyme cleavage sites in the novel gene to facilitate its construction, or serve as a peptide spacer between the domains, or serve as a flexible peptide linker or provide another function. Preferably the domains are separated by a flexible linker.

Two or more different genes encoding different SCMs may be used to achieve improved co-stimulation, or both co-stimulation of naive T-cells and induction of memory responses. For example a gene encoding an SCM containing the B7-1 extracellular domain may be administered with a gene encoding an SCM containing the B7-2 extracellular domain.

Thus in one aspect of the invention, there is provided one or more genetic vectors capable of expressing in mammalian cells one or more secreted co-stimulatory molecules, each secreted co-stimulatory molecule comprising at least one antigen-binding domain and at least one domain from the extracellular portion of a cell-surface co-stimulatory molecule. The co-stimulatory domain may be obtained from a molecule expressed on the surface of an antigen-presenting cell such as a B7 family member. Preferably the co-stimulatory domain is from B7-1, B7-2 or B7-3. Most preferably it is comprised of B7-1 amino acid residues 1 to approximately 215 of the mature B7-1 molecule (described in WO-A-96/00092) or amino acids 1 to approximately 225 of the mature cell-surface form of B7-2 (described in Gerstmeyer et al. 1997 J. Immunol. 158:45844590).

The genetic vector according to this aspect of the invention comprises at least a promoter and enhancer for expression in mammalian cells and a polyadenylation site. Suitable promoters and enhancers include the MIE promoter-enhancer from human cytomegalovirus or promoters which are expressed preferentially in cells present within the tumour. Such promoter-enhancers include those from the MUC1 gene, the CEA gene or the 5T4 antigen gene. If two or more SCMs are expressed, the coding regions for these may be inserted into two separate vectors or a single vector may be used to express the two or more genes. In the latter case each gene is provided with a separate copy of the promoter, or an internal ribosome entry site (IRES) is used to separate the two coding sequences.

Effector Domains

The antibody and/or the POI of the present invention may also contain one or more effector domains.

The effector domain or domains may be activated on binding of the antibody to a cell surface molecule ("CSM") leading to inhibition of cell proliferation, survival or dissemination. The CSM in this aspect of the invention is a cell surface molecule for which a specific TBP is available such as a tumour specific carbohydrate moiety, an oncofoetal antigen, a mucin, a growth-factor receptor or another glycoprotein. The CSM is preferably an antigen restricted in its tissue distribution (for example, it may be restricted to tumour cells). In some instances, the CSM is not shed from the cell surface into the circulation to an appreciable extent. However, shedding may occur. By way of example, shedding of the 5T4 antigen into the stroma can serve to further localise the NOI and/or the POI to the tumour environment.

The effector domain of the present invention may possess enzymatic activity and may be for example a pro-drug activating enzyme, or it may be a non-enzyme domain. Examples of antibodies containing effector domains with enzyme activity include antibody—enzyme conjugates or fusions. Antibody—enzyme conjugates have been described including conjugates with alkaline phosphatase (Senter et al, 1988 Proc. Natl. Acad. Sci. 85: 48424846); carboxypeptidase G2 (Bagshawe et al. 1988 Br. J. Cancer 58: 700703); P-lactamase (Shepherd et al 1991 Bioorg. Med. Chem. Left. 1:21-26); and Penicillin-V-amidase (Kerr et a!. 1990 Cancer Immunol. Immunother. 31: 202-206. Antibody—enzyme fusions have also been described (Goshom et al 1993 Cancer Res 53: 2123-2127; Wels et al 1992 Bio/Technology 10: 1128-1132). Each of these examples can be used in this aspect of the invention. Additional or alternative enzymes which may be included in antibody-enzyme fusions include human Carboxypeptidase Al or a mutant thereof (Smith et a! 1997 J. Biol. Chem. 272: 15804-15816); cytosine deaminase (Mullen et al., 1994 Cancer Res. 54: 1503-1506); HSV thymidine kinase (Borrelli et al. 1988 Proc. Natl. Acad. Sci. 85: 7572-7576.); nitroreductase; P450-Reductase and a P450.

Preferably the pro-drug activating enzyme domain or domains are genetically fused to the C-terminus of an immunoglobulin or immunoglobulin domain such as a scfv or a single-chain antibody or Fab-fragment. In a particularly preferred embodiment of this aspect of the invention, the immunoglobulin domain or domains are human or humanised and the enzyme is a human enzymp—such as a Carboxypeptidase a P450 or P450-Reductase. The enzyme may be a mutant enzyme which converts a pro-drug more efficiently than does the native human enzyme. In accordance with the present invention, any enzyme that has utility in an ADEPT strategy can be used.

In each case, a suitable pro-drug is used in the treatment of the patient in combination with the appropriate pro-drug activating enzyme. Examples of pro-drugs include etoposide phosphate (used with alkaline phosphatase Senter et al., 1988 Proc. Nat. Acad. Sci. 85: 4842-4846); 5-fluorocytosine (with Cytosine deaminase Mullen et al. 1994 Cancer Res. 54: 1503-1506); Doxorubicin-N-p-hydroxyphenoxyacetamide (with Penicillin-V-Amidase (Kerr et al. 1990 Cancer Immunol. Immunother. 31: 202-206); Para-N-bis(2chloroethyl) aminobenzoyl glutamate (with Carboxypeptidase G2); Cephalosporin nitrogen mustard carbamates (with P-lactamase); SR4233 (with P450 Reducase); Ganciclovir (with HSV thymidine kinase, Borrelli et al. 1988 Proc. Natl. Acad. Sci. 85: 7572-7576) mustard pro-drugs with nitroreductase (Friedlos et al. 1997 J Med Chem 40: 1270-1275) and Cyclophosphamide (with P450 Chen et al. 1996 Cancer Res 56: 1331-1340).

Alternatively the effector domain may be a non-enzyme domain. Examples of non-enzyme effector domains include toxins such an exotoxin from a pseudomonad bacterium, all or part of a cytokine such as IL-2 or IFNγ, or effector domains from immunoglobulin heavy chains.

In a preferred embodiment of this aspect of the invention, the antibody or POI contains an effector domain capable of activating macrophage FcgR I, II or III receptors. On binding of the TBP to antigen on the tumour cells, macrophages present within the hypoxic regions of the tumour are activated to destroy the tumour cells directly by phagocytosis or ADCC or are activated to secrete pro-inflammatory cytokines which serve to enhance the natural immunological response to the tumour. The antibody or POI may contain an Fc region from an immunoglobulin, a mutant Fc region, a receptor-binding fragment of the Fc region or may contain another FcR—binding domain.

Preferably the antibody or POI contains an entity, preferably an effector domain entity, that confers protein stability ex vivo and/or in vivo.

In accordance with the present invention, the antibody or POI may be or include an intact Fc region from an IgG, (such as human IgG1 or IgG3, or a part thereof.

In one preferred embodiment of this aspect of the invention, the antibody or POI is a Sab (single chain antibody) containing a human IgG1 constant region and a binding domain which recognizes the 5T4 antigen.

In a particularly preferred embodiment of this aspect of the invention, the antibody or POI is a Sab (single chain antibody) containing a human IgG constant region and a binding domain which recognizes the 5T4 antigen.

The effector domain may be encoded by a portion of a cDNA fused in-frame to the DNA encoding the antibody or POI. Alternatively a genomic fragment containing introns may be used such as a human IgG1 heavy chain constant region genomic fragment.

Here the term "intron" is used in its normal sense—e.g. an intervening sequence of DNA within a gene which is removed by RNA splicing and so is not present in the mature messenger RNA and does not code for protein. Introns can be conditional or alternatively spliced in different cell types.

Introduction of antibody and/or NOI genes into monocytes or macrophages may be combined with further treatments to elicit macrophage differentiation and activation. For example, cells maintained ex vivo may be treated with cytokines such as IFNγ, CSF-1 or GM-CSF prior to re-introduction into the patient. Alternatively, genes encoding these cytokines may be introduced into the monocytes/macrophages in the same or a different vector system in vivo or ex vivo. Consequently in a still further aspect of the invention there is provided a method of treating a disease in a mammal which comprises administering to an individual a combination of a cytokine or a cytokine-encoding gene and one or more antibody genes.

Additional Functional Component

The antibody and/or the NOI may further comprise at least one additional functional component.

Preferably the additional functional component is selected from any one or more of a signalling entity (such as a signal peptide), an immune enhancer, a toxin, or a biologically active enzyme.

In a preferred aspect the POI is a secretable POI. Thus, in this aspect of the present invention, preferably, the additional functional component is at least an entity capable of causing the POI to be secreted—such as a signalling entity.

The NS and/or NOI may also comprise an additional functional component, such as a promoter.

The term "promoter" is used in the normal sense of the art, e.g. an RNA polymerase binding site in the Jacob-Monod theory of gene expression.

Preferably the vector system comprises a tumour specific promoter enhancer.

Other preferred additional components include entities enabling efficient expression of the antibody and/or POI. For example, the additional component may be an enhancer. Here, the term enhancer includes a DNA sequence which binds to other protein components of the transcription initiation complex and thus facilitates the initiation of transcription directed by its associated promoter.

As well as promoter(s) and/or enhancer(s) the NS or NOI may comprise translation initiation signals, internal ribosome entry sites (IRES), splicing and polyadenylation signals.

The promoter and/or enhancer may be tissue-restricted in its activity. For example a tumour-specific promoter-enhancer, such as a 5T4 antigen gene promoter-enhancer or the CEA-gene promoter-enhancer may be used. Alternatively, or additionally, an element or elements for regulated expression may be present, such as a hypoxia regulated enhancer. An example of a hypoxia regulated expression element (HRE) is a binding element for the transcription factor HIF-1. The enhancer elements or elements conferring regulated expression may be present in multiple copies. Preferably, expression of the or a gene (such as a therapeutic gene) is inducible by hypoxia (or low oxygen supply) such as may be found in a tumour mass. Most preferably, the promoter and/or enhancer directing expression of the gene (such as a therapeutic gene) contains both hypoxia-responsive elements and elements which give higher expression in tumour cells than in neighbouring non-tumour cells.

Pharmaceutical Compositions

The present invention also encompasses a pharmaceutical composition for treating one or more individuals by gene therapy, wherein the composition comprises a therapeutically effective amount of the vector system according to the present invention. The pharmaceutical composition may be for human or animal usage. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The invention will now be further described by way of examples, which are meant to serve to assist one of ordinary skill in the art in carrying out the invention and are not intended in any way to limit the scope of the invention. Reference is made to the following Figures:

FIG. 1a—which shows a DNA sequence encoding a 5T4 scFv, designated 5T4scFv.1. The sequence of the mature secreted protein is given.

FIGS. 1b-1d—which show the cDNA sequence encoding 5T4Sab1. The sequence begins with a HindIII restriction site followed by a translation initiation signal and a signal peptide.

FIGS. 2a-2b—which show the sequence of B7-1.5T4.1

Figure 3B:
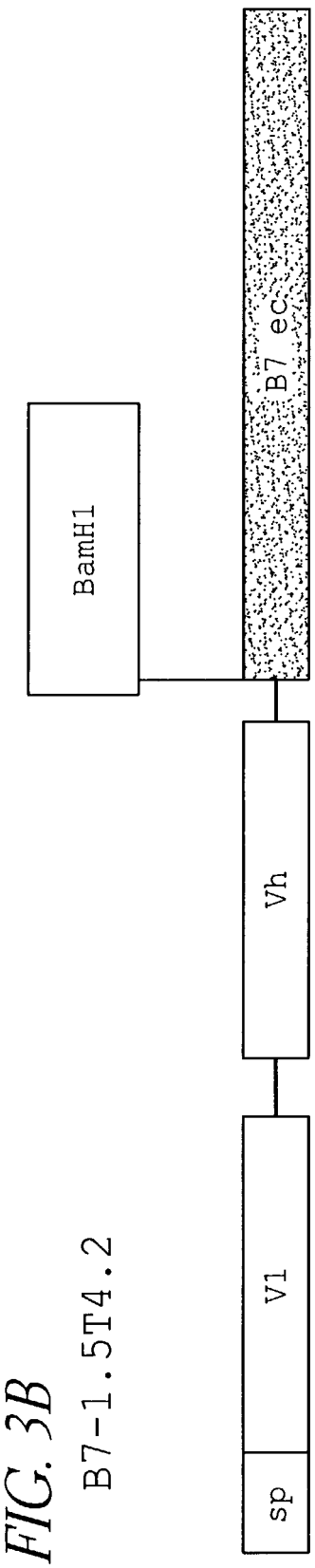

FIG. 3—which shows a diagrammatic representation of two SCMs based on the B7-1 co-stimulatory domain; FIG. 3a shows the SCM B7-1.5T4.1 and FIG. 3b shows B7-1.5T4.2 in which the order of the co-stimulatory and tumour-binding domains are reversed. Sp=signal peptide; B7 ec=extracellular domain of B7-1; Vl=light chain variable domain of 5T4; Vh=heavy chain variable domain of 5T4.

FIG. 4—which shows the sequence of the extracellular domain of human B7-2, including the signal peptide sequence. The mature protein begins at amino acid 17. The B7-2 derived sequence is followed by a flexible linker gly-gly-gly-gly-ser (SEQ ID NO:28).

Figure 5:
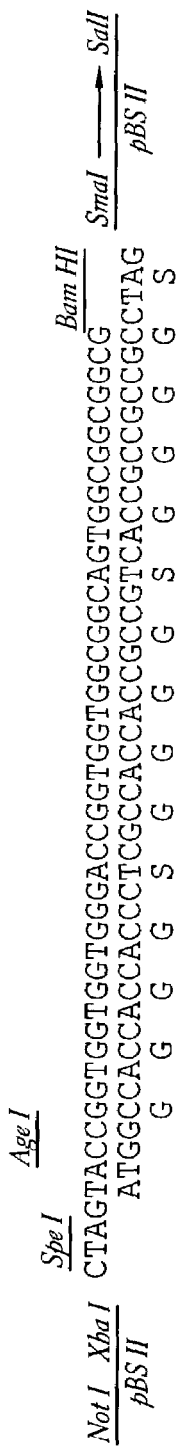

FIG. 5—which shows pKLink—linker in pBluescript II SK (pBS II) wherein the linker is three copies of the amino-acid ssequence gly-gly-gly-gly-ser (SEQ ID NO:28).

Figure 6:
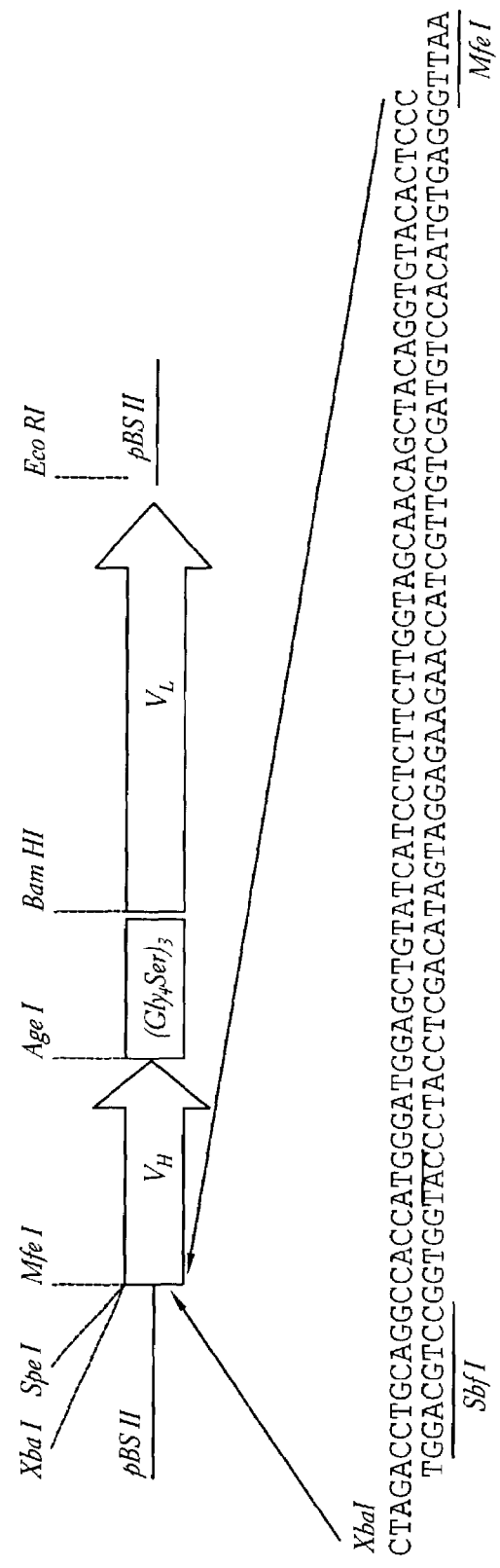
Figure 7:
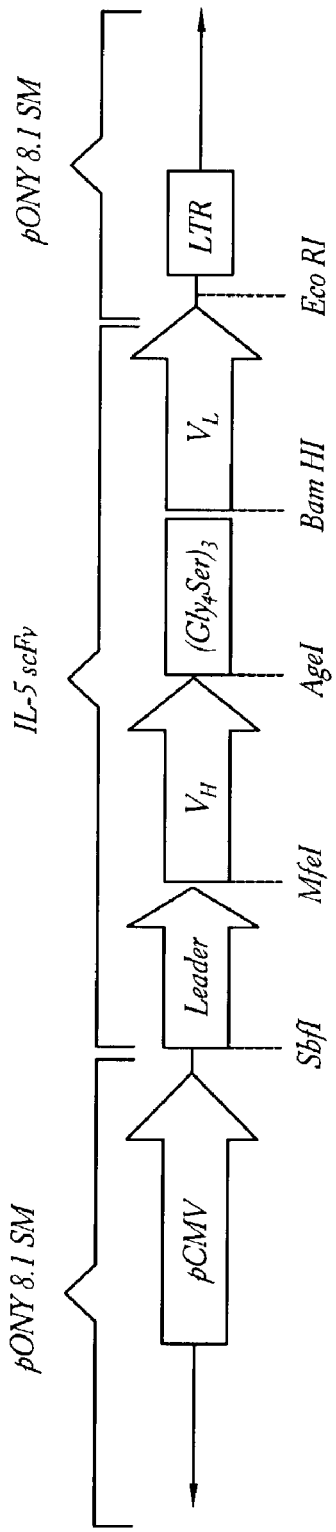
Figure 8:
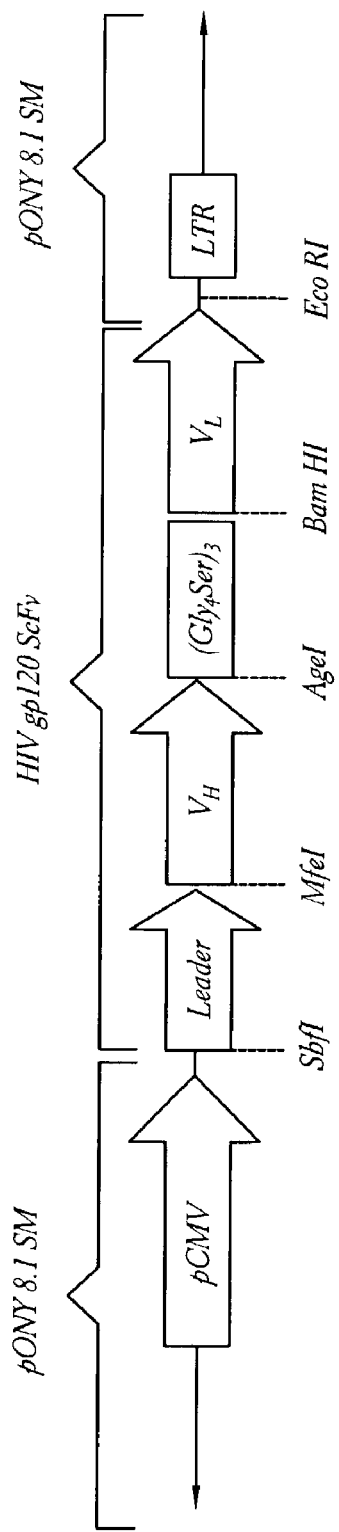
Figure 9:
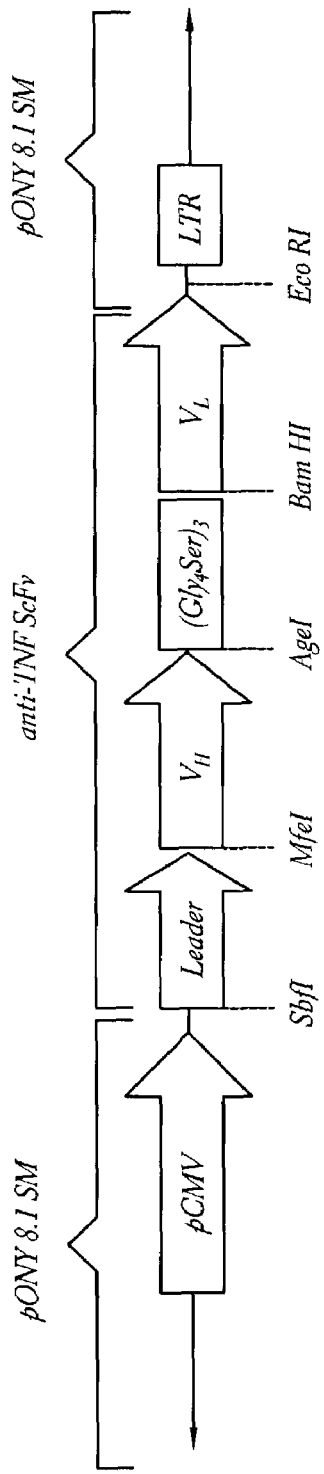
Figure 10:
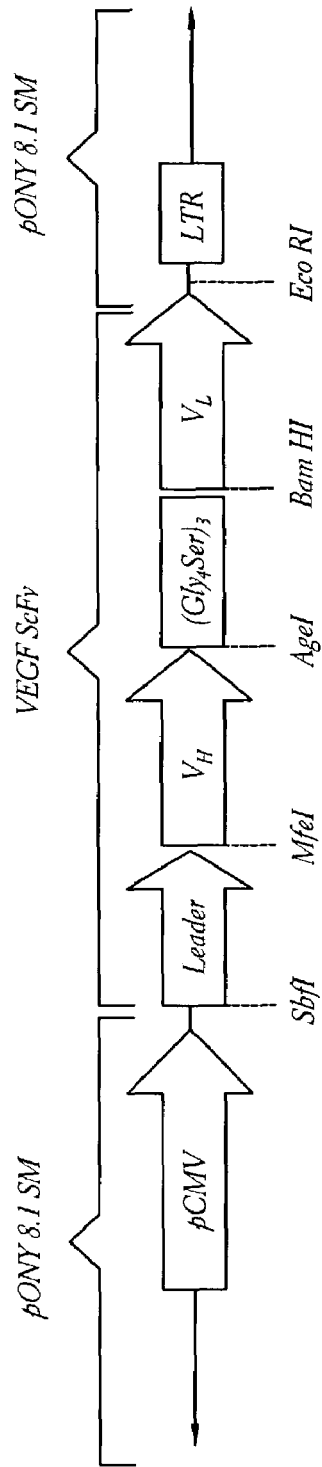

FIG. 6—which shows anti-TNF alpha scFv in pBSII and subsequent addition of the leader sequence FIG. 7—which shows Leader-IL-5 scFv in pONY 8.1SM FIG. 8—which shows Leader-HIV gp120 scFv in pONY 8.1SM FIG. 9—which shows Leader-anti-TNF alpha scFv in pONY 8.1SM FIG. 10—which shows Leader-VEGF scFv in pONY 8.1SM FIG. 11: Immunostain of CT26-h5T4 tumours injected with Adlac z FIG. 12: Immunostain of CT26-h5T4 tumours injected with AdB7-scFv

EXAMPLES

Example 1

Construction of 5T4 Sab and Retroviral—Vector Delivery to Tumour

The cDNA encoding the murine 5T4 monoclonal antibody is cloned and sequenced by standard techniques (Antibody engineering: a practical approach ed McCafferty et al. 1996 OUP). The sequence of the variable region of the antibody can be used to construct a variety of immunoglobulin-like molecules including scFvs. The coding sequence of a 5T4 scFv, 5T4scFv.1, is shown in FIG. 1a. In this molecule, the DNA sequence encodes the Vh from the mouse 5T4 monoclonal antibody followed by a 15 amino acid flexible linker and the Vl region of the mouse 5T4 antibody. The flexible linker encodes 3 copies of the aminoacid sequence gly-gly-gly-gly-ser (SEQ ID NO:28) and the DNA sequence similarity between the repeats has been minimized to avoid the risk of recombination between the repeats when plasmids containing them are grown in E. coli.

The DNA sequence shown in FIG. 1a can also be used to construct a variety of single-chain antibodies (Sabs) by coupling scFv-encoding sequences to a sequence encoding a Fc region to form an in-frame fusion. A Sab is constructed using a series of DNA cassettes which can be independently varied to suit particular purposes.

Cassette 1—Translation Initiation Signal and Signal Peptide

In order to achieve correct translation initiation and secretion from mammalian cells, the following sequence is used:

aagcttCCACCATGGGATGGAGCTGTATCATCCTCTTCTTGGTAGCAACA
GCTACAGGTGTCCACTCC

This contains a convenient HindIII restriction site for cloning into expression vectors (lower case), the consensus translation initiation signal for mammalian cells (ANNATGPu) and the coding sequence for a signal peptide sequence from an immunoglobulin gene.

Cassette 2—scFv

The sequence of the secreted portion of the 5T4scFv.1 is shown in FIG. 1a. This molecule can be represented as Vh-linker-Vl, wherein the linker is three copies of the amino-acid sequence gly-gly-gly-gly-ser (SEQ ID NO:28).

5T4 scFv2 consists of the 5T4 variable region sequences connected in the order Vl—flexible linker Vh. In this case the linker encodes the 20 amino-acid peptide of four copies of the amino-acid sequence gly-gly-gly-gly-ser (SEQ ID NO:28). A longer linker improves assembly of the scFv when the V-region segments are in this order. (Pluckthun et al in Antibody Engineering: a practical approach, ed McCafferty et al. 1996 OUP).

Cassette 3—Heavy Chain Constant Region

The sequence of a human g1 constant region genomic clone is given in Ellison et al. 1982 Nucl. Acids res. 10: 4071-4079. This sequence contains constant-region introns in addition to the coding sequence. This is fused in-frame to the 3'-end of one of the scFv sequences from Cassette 2. Vectors for convenient assembly of such constructs are described (Walls et al. 1993 Nucl. Acids Res. 21:2921-2929.

A cDNA of a 5T4 Sab, designated 5T4Sab1 is shown in FIG. 1b, containing cassettes 1, 2 and 3.

For expression of a 5T4-specific scFv or Sab in human cells, the coding sequence is inserted into the vector pClneo (Promega) under the control of a strong promoter and polyadenylation signal. The translation initiation signal and immunoglobulin leader (signal peptide) sequence from Cassette 1 at the 5'end of the coding region ensure efficient secretion of the scFv or Sab from mammalian cells.

For expression of an intact Ig, two separate translation cassettes are constructed, one for the heavy chain and one for the light chain. These are separated by an internal ribosome—entry site (IRES) from the picornavirus FMDV (Ramesh et al. 1996 Nucl. Acids Res. 24: 2697-2700. Alternatively, each cDNA is expressed from a separate copy of the hCMV promoter (Ward and Bebbington 1995 In Monoclonal Antibodies ed Birch and Lennox Wiley-Liss).

For production of retrovirus capable of expressing 5T4 antibody or immunoglobulin-like molecules with 5T4 specificity, the gene encoding a 5T4-based Sab, or a dicistronic message encoding heavy and light chains, is inserted into a retroviral vector in which retroviral genomic transcripts are produced from a strong promoter such as the hCMV-MIE promoter. A suitable plasmid is pHIT111 (Soneoka et al. 1995 Nucl. Acids Res.23; 628-633) and the required gene is inserted in place of the LacZ gene using standard techniques. The resulting plasmid, pHIT-5T4.1 is then transfected into the FLYRD18 or FLYA13 packaging cell lines (Cosset et al. 1995 J. Virol. 69; 7430-7436) and transfectants selected for resistance to G418 at 1 mg/ml. G418-resistant packaging cells produce high titres of recombinant retrovirus capable of infecting human cells. The virus preparation is then used to infect human cancer cells and can be injected into tumours in vivo. The 5T4 Sab is then expressed and secreted from the tumour cells.

In pHIT111, the MoMLV LTR promoter-enhancer is used for expression of the therapeutic gene in the target cell. The vector can also be modified so that the therapeutic gene is transcribed from an internal promoter-enhancer such as one which is active predominantly in the tumour cells or one which contains a hypoxia regulated element. A suitable promoter is a truncated HSV TK promoter with 3 copies of the mouse PGK HRE (Firth et al., 1994 Proc. Natl. Acad. Sci. 91: 6496-6500).

Example 2

Transfection of Macrophages/Monocytes with an Expression Vector Encoding TBP

Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (eg Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing TBP in human cells. For constitutive high level expression, the TBP is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al., 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (eg using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 3

Assay for ADCC Mediated by Macrophages

Cells from primary human tumours or tumour cell lines which have been transduced with retrovirus expressing TBP are mixed with autologous or heterologous human macrophages, prepared as described in Example 2, for analysis of ADCC activity mediated by the TBP. Alternatively, macrophages engineered to produce TBP as described in Example 2 can be used to direct ADCC on non-transduced tumour cells.

The assay is carried out according to standard procedures (Sandlie and Michaelsen 1996 In Antibody engineering: a practical approach. Ed McCafferty et al. Chapter 9) with appropriate modifications. Briefly, the effector cells (macrophages or freshly isolated monocytes) are suspended at $3 \times 10^6$ cells/ml in the appropriate tissue culture medium (DMEM/Hepes, obtained from Life Technologies, containing 1% Foetal Calf Serum). $3 \times 10^5$ tumour target cells, labelled with $^{51}Cr$ are placed in each well of a round-bottomed microtitre plate in 0.1 ml culture medium. (Note the culture medium can include spent medium from the cells producing the TBP). 50 ml effector cells are added to the wells, the plate is centrifuged at 300 g for 2 min and incubated at 37° C. for varying periods (eg 4 h) in a tissue culture incubator. The supernatant is then harvested by centrifugation and counted in a gamma counter. Results are expressed as percent lysis relative to total chromium release from an equivalent sample of target cells lysed with 0.1% Tween-20. The effector: target cell ratio can be varied in the assay to produce a titration curve.

For the prior stimulation of macrophage differentiation or priming, cytokines are added to the cultures. IFNg (Sigma) is added at between 100 and 5000 U/ml. CSF-1 or GM-CSF (Santa Cruz Biotechnology) can also be added at appropriate concentrations.

Example 4

Analysis of Efficacy in Animal Models

Human tumour-derived cell lines and tissues are cultured in vivo in genetically immunodeficient, "nude" mice according to well established techniques (see for example Strobel et al. 1997 Cancer Res. 57: 1228-1232; McLeod et al. 1997 Pancreas 14: 237-248). Syngeneic mouse models, in which a syngeneic tumour line is introduced into an immunocompetent mouse strain may also be used. These serve as suitable animal models for evaluating gene delivery systems of the invention. Vectors or engineered cells are administered systemically or directly into the tumour and tumour growth is monitored in treated and untreated animals. This system is used to define the effective dose range of the treatments of the invention and the most appropriate route of administration.

Example 5

Construction of B7—scFv Fusion Proteins

The extracellular domain of B7-1 is defined by aminoacid residues 1-215 of the native human B7-1 protein. This sequence, together with its signal peptide-encoding sequence, is used to construct secreted fusion proteins which also contain the scFv derived from the 5T4 monoclonal antibody. The sequence of the 5T4 scFv is given in FIG. 1a.

A DNA coding sequence is constructed using standard molecular biology techniques which encodes a fusion protein in which the N-terminus of the 5T4 scFv is fused after amino acid 215 of human B7-1. The sequence of this coding sequence, B7-1.5T4.1, is shown in FIG. 2. The fusion protein contains a flexible (gly-gly-gly-gly-ser, (SEQ ID NO:28)) spacer between the B7-1 and 5T4 scFv sequences.

The introduction of a convenient BamH1 restriction site at the end of the linker insertion (beginning at nucleotide 733) also allows for further linkers to be screened for optimal expression of bi-functional fusion protein. FIG. 3 indicates the fusion protein in diagrammatic form. It is similarly possible to construct B7-1.5T4.2 (FIG. 3b) in which the scFv is N-terminal and the B7 extracellular domain is C-terminal. In this case only the coding sequence of the mature B7-1 (without signal peptide) is required. A signal peptide such as an immunoglobulin leader sequence is added to the N-terminus of the scFv in this instance.

For fusion proteins which use the co-stimulatory extracellular domain of B7-2, the signal peptide and extracellular domain of B7-2 is used in place of B7-1 sequences. FIG. 4 shows the coding sequence of the SCM B7-2.5T4.1costimulatory domain. It encodes the first 225 amino acids of human B7-2, preceded by its signal peptide, and a flexible linker (gly-gly-gly-gly-ser, SEQ ID NO:28). The BamHI site at is 15 the end of this sequence can be used to insert the domain upstream of the 5T4scFv.1 (see FIG. 3). The sequence includes the B7-2 signal peptide which can serve to allow secretion of this fusion protein in which the B7-2 domain is at the N-terminus of the fusion protein.

Each engineered cDNA is inserted into the mammalian expression vector pCI to allow expression in mammalian tissue culture cells. For this purpose, a linker sequence is added to the 5'-end of the coding sequence which introduces a convenient restriction site for insertion into the polylinker of pCI and adds the translation initiation signal CCACC immediately adjacent to the first ATG codon. Constructs in pCI are transfected into a suitable mammalian host cell line such as COS-1 to confirm secretion of the SCM. The transcription cassette from pCI or an appropriate segment of the transcription cassette is subsequently sub-cloned into the expression vector to be used as the gene delivery system for therapeutic use.

Example 6

Transfection of Macrophages/Monocytes with an Expression Vector Encoding an SCM Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (eg Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing SCM in human cells. For constitutive high level expression, the SCM is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (eg using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 7

Analysis of SCM Binding to CTLA-4 and 5T4-Antigen Expressing Cells

The B7-1 or B7-2 domains are expected to bind specifically to CD28 and CTLA-4 present on human T-cells. Binding to T-cells or Chinese hamster ovary cells transfected with human CTLA-4 or CD28 is determined using FACS analysis as follows. $5 \times 10^5$ CTLA-4 expressing target cells or equivalent cells lacking CTLA-4 (untransfected CHO cells) are incubated with 0.1 ml culture supernatant from COS-1 cells transiently transfected with SCM genes for 1 h at 4° C. The cells are washed and incubate with 1 mg monoclonal antibody specific for the B7 domain (eg Mab 9E10) followed by FITC-labelled goat anti-mouse IgG (Pharmingen) and analysis by FACS.

Binding of scFv to 5T4-antigen is similarly assessed using target cells expressing 5T4-antigen (5T4-transfected A9 cells) or control cells (A9).

Example 8

Analysis of Co-stimulatory Activity

An established mouse cell line of Balb/c origin such as HC11 cells is transfected with the cDNA encoding human 5T4-antigen (Myers et al. 1994 J. Biol. Chem. 269; 9319-9324) inserted in the expression vector pClneo.

Splenic T-cells from Balb/c mice are isolated by standard procedures (Johnstone and Thorpe 1996 In Immunochemistry in Practice. Blackwell. Chapter 4). T-cells are pre-stimulated by incubation for 1-2 days in medium containing 10 ng/ml PMA (Sigma) and 100 U/ml human IL-2 (Boehringer Mannheim). HC11-5T4 cells are incubated at $10^4$ cells/well of a 96-well tissue culture tray for 2 h with up to 0.1 ml supernatant from COS cells transfected with SCM gene. Up to $10^5$ pre-stimulated T-cells are added to each well, the cells are pulsed with 0.25 mCi/well $^3$H-thymidine and incorporation of $^3$H4 hymidine is measured using a liquid scintillation counter after 24 h.

Incorporation of $^3$H-thymidine is anticipated to be enhanced by the presence of SCM.

Example 9

Analysis of Co-stimulation in Animal Models

HC11 cells transfected with the human 5T4-antigen gene (Example 4) are grown as tumours in Balb/c mice. SCM genes B7-1.5T4.1 or B7-2.5T4.1 or a combination of both genes are introduced into the tumour cells prior to implantation and the growth of the tumours and the growth of control tumours which do not express SCM genes in vivo are monitored.

It is believed that the expression of SCM genes lead to significant reduction in tumour growth.

Example 10

Construction of a B7-1/ScFv, Specific for Human 5T4, Fusion Protein

Standard molecular biology techniques are used to construct a fusion protein consisting of the leader sequence and extracellular domain of B7-1, fused via a flexible linker to the $V_H$ and $V_L$ of the murine Mab 5T4 specific to human 5T4.

The flexible linker, used to join the extracellular domain of B7.1 and the ScFv, was constructed by annealing two homologous oligonucleotides with engineered 5' SmaI and 3' SpeI sites—using oligonucleotides upper

```
5' GGG GGT GGT GGG AGC GGT GGT GGC GGC AGT GGC GGC
GGC GGA A 3'
(SEQ ID NO:12)
``` and lower

```
5' CTA GTT CCG CCG CCG CCA CTG CCG CCA CCA CCG CTC
CCA CCA CCC CC 3'
(SEQ ID NO:13)
```

The linker is cloned into pBluescript (Stratagene) via SmaI and SpeI to produce pLiNK. The signal peptide (sp) and extracellular domain of murine B7.1 were amplified by PCR from pLK444-mB7.1 (supplied by R. Germain NIH, USA) via primers that introduce 5' EcoRi and 3' SmaI sites—primers - forward
```
5' C TCG AAT TCC ACC ATG GCT TGC AAT TGT CAG TTG
ATG C 3'
(SEQ ID NO:14)
``` reverse

```
5' CTC CCC GGG CTT GCT ATC AGG AGG GTC TTC 3'
(SEQ ID NO:15)
```

The B7.1 PCR product was cloned into pLINK via EcoRI and SmaI to form pBS/B7Link.

The $V_H$ and $V_L$ of the 5T4 specific ScFv was amplified via primers-forward primer
```
5'CTC ACT AGT GAG GTC CAG CTT CAG CAG TC 3'.
(SEQ ID NO:16)
``` reverse primer

```
5'CTC GCG GCC GCT TAC CGT TTG ATT TCC AGC TTG GTG
CCT CCA CC 3'.
(SEQ ID NO:17)
``` that introduce 5' SpeI and 3' NotI sites from pHEN1-5T4 ScFv. PBS/B7Link was digested with SpeI and NotI and ligated with the ScFv to form OBM 233 consisting of the sequence shown as SEQ ID NO:5: B7 Link scFv sequence.

This fusion can be used to construct a recombinant vector e.g. retrovirus, Lentivirus, adenovirus, poxyirus, vaccinia virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to a pronounced increase in IL-2 which promotes CD8 (cytotoxic T cell) expansion (Linsley P S, Brady W, Grosmaire L, Aruffo A, Damle N K, Ledbetter J A J Exp Med 1991 March 1;173 (3):721-730 Binding of the B cell activation antigen B7 to CD28 costimulates T cell proliferation and Il-2 mRNA accumulation.) Tumour cells that have been B7 tranfected with B7 have been shown retardation in animal models (Townsend S E, Allison J P Science 1993 15;259(5093): 368-370).

Example 11

Transient Expression and Purification of B7-1/ScFv and LScFv

For transient expression of B7-1/ScFv the human CMV expression plasmid pCIneo (Promega) was used. B7/ScFv was excised from OBM 233 by digestion with EcoRI/NotI and cloned into pCIneo that was previously digested with EcoRI/NotI. Transient expression of recombinant protein is made by transfection of 293T cells with the relevant plasmid using calcium phosphate (Profectin, Promega). Conditions used were similar to those recommended by the manufacturer. To reduce bovine serum contamination serum free optimum media (Gibco BRL). After 36-48 hours transfection supernatants were harvested and spun through a Centriprep (Amicon, Glos. UK) 10 filter (all proteins larger than 10 kDa are purified/concentrated) and a Centricon (Amicon) 10 filter. Supernatants are concentrated approximately 30 fold.

For B7-1 to be biologically functional it must be able to display binding with one of it's natural ligands either CTLA-4 or CD28 found on the surface of specific populations of T cells (e.g CD4+). The biological activity B7-1/ScFv fusion protein was analysed for simultaneous interaction with its natural ligand CTLA-4 (in the form of CTLA4-Ig supplied by Ancell, Minn., USA) and A9 cells expressing human 5T4. Briefly: approximately 5×10⁵ A9-h5T4 cells were incubated with 100 ul of either B7.1/ScFv or LScFv supernatant in a U bottom 96 well plate at 4° C. for 1 hour. After washing cells were incubated with CTLA4-Ig (Ancell) for 1 hour. After washing, bound CTLA4-Ig was detected using an FITC conjugated anti-mouse Ig (Dako).

Results show obvious binding of CTLA-Ig with the B7-1 extracellular domain, bound via the ScFv, to the surface of human 5T4 positive A9 cells. The lack of binding activity with 5T4 negative A9 cells further illustrates that the interaction of B7 with CTLA4-Ig and ScFv with 5T4 are specific.

Example 12

ScFv-IgG Fusion Example

Construction of ScFv-IgG

The sequence encoding a translation initiation sequence and the human immunoglobulin kappa light chain signal peptide is synthesized as two complementary single stranded oligonucleotides which when annealed also contain an internal XhoI site at the 5' end and in addition leave a XbaI compatible 5' overhang and a PstI compatible 3' overhang

```
ctagactcgagCCACC ATG GGA TGG AGC TGT ATC ATC CTC
TTC TTG GTA GCA ACA GCT ACA GGT GTC CAC TCC GAG
GTC CAG ctgca
(SEQ ID NO:18)
``` and

```
g CTG GAC CTC GGA GTG GAC ACC TGT AGC TGT TGC TAC
CAA GAA GAG GAT GAT ACA GCT CCA TCC CAT GGTGGctcga
gt.
(SEQ ID NO:19)
```

This is then cloned into pBluescript II (Stratagene) restricted with XbaI and PstI to create pBSII/Leader.

The 5T4 scFv is amplified by PCR from pHEN1 using oligonucleotides which incorporate a PstI site at the 5' end of the product and a HindIII at the 3' end

```
        GTC CAG CTG CAG CAG TCT GG
        (SEQ ID NO:20)
``` and

```
        CG TTT GAT TTC AAG CTT GGT GC.
        (SEQ ID NO:21)
```

This is then restricted with those enzymes and inserted into pBSII/Leader restricted with the same enzymes, creating pBSII/Leader/scFv.

The HIgG 1 constant region is amplified by PCR from the cloned gene using oligonucleotides which incorporate a HindIII site at the 540 end and a XhoI site at the 3' end

```
gcgc AAG CTT gaa atc aaa cgg GCC TCC ACC AAG GGC
CCA
(SEQ ID NO:22)
``` and

```
gcgc ctcgag TCA TTT ACC CGG AGA CAG GG
(SEQ ID NO:23)
```

This is then restricted with those enzymes and inserted into pBSII/Leader/scFv restricted with the same enzymes, creating pBSII/Leader/scFv/HG1. The sequence for this construct is shown in the Figures.

This fusion can be used to construct a recombinant vector e.g. retrovirus, Lentivirus, adenovirus, poxyirus, vaccinia virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). Bound IgG will promote specific tumour destruction via a collection of mechanisms collectively known as antibody dependent cellular cytotoxicity (Munn et al Can res 1991 ibid, Primus et al 1993 Cancer Res ibid).

Example 13

Construction of ScFv-IgE1 (Human IgE1 Heavy Constant Region)

A similar fusion construct of 5T4 scFv—human IgE constant heavy chain is made consisting of the sequence shown as SEQ ID NO:6.

The fusion construct is made by amplifying the human IgE1 constant heavy region by PCR cDNA derived from human B-cells RNA by RT and subsequently using oligonucleotides which incorporate a HindIII site at the 5' end and a XhoI site at the 3' end

```
gcgc AAG CTT gaa atc aaa cgg GCC TCC ACA CAG AGC
CCA
(SEQ ID NO:24)
``` and

```
gcgc ctcgag TCA TTT ACC GGG ATT TAC AGA.
(SEQ ID NO:25)
```

This is then restricted with those enzymes and inserted into pBSII/Leader/scFv restricted with the same enzymes, creating pBSII/Leader/scFv/HE1.

As described above the ScFv-IgE construct can be incorporated into a recombinant viral vector for use in gene therapy of cancer e.g. inject patient tissue directly or to transduce patient derived macrophages/moncytes/CD34+ cells ex vivo. The fusion protein will be secreted and will bind to tumour cells bearing the antigen that the ScFv is specific for. Binding of IgE to tumour cells should promote a strong histamine response via activation of mast cells. This will lead to a strong inflammatory response and destruction tumour cells as is reported for IgE cytotoxic destruction of parasites e.g. helminth larvae (Capron M 1988 Eosinophils in diseases: receptors and mediators. In progress in allergy and clinical immunology (Proc. $13^{th}$ Int. Congress of Allergy and Clinical Immunology) Hogrefe & Huber Toronto p6). Such inflammation and tumour destruction should initiate the recruitment of other immune effector cells. Past reports indicate that treatment with an MMTV antigen specific IgE Mab leads to protection from a tumour expressing MMTV antigen (Nagy E Istanvan B, Sehon A H 1991 Cancer Immunol. Immunotherapy vol 34:63-69).

Example 14

Construction of B7/EGF

B7-EGF Synthetic Gene.

A fusion construct of B7—EGF is made by inserting a PCR product amplified from the region of the gene encoding the mature EGF peptide (see accession number X04571) into pBS/B7 Link. This construct has the sequence shown as SEQ ID NO:7.

Using cDNA derived by RT of RNA isolated from a cell line such the 293 human kidney line (ATCC: CRL1573), the DNA is amplified by PCR using oligonucleotides containing a SpeI restriction enzyme site at the N-terminus and a stop codon and a NotI site at the C-terminus

```
GG ACT AGT AAT AGT GAC TCT GAA TGT CCC
(SEQ ID NO:26)

and

ATT AGC GGC CGC TTA GCG CAG TTC CCA CCA CTT C
(SEQ ID NO:27)
```

The resulting product is digested with those enzymes and ligated to pBS/B7 Link which has been restricted with the same enzymes creating pBS/B7 Link EGF. The B7 Link EGF cassette is then excised with EcoRI and NotI and inserted into a derivative of pHIT111 (Soneoka et al., 1995, Nucl Acid Res 23; 628) which no longer carries the LacZ gene An alternative to using ScfV is to use growth factors that have a high affinity to their corresponding receptor e.g. epidermal growth factor which binds to several receptors including erb-2 which is highly associated with tumourgenesis.

As described above the fusion construct can be incorporated into a recombinant viral vector for use in gene therapy e.g. inject patient tissue directly or to transduce patient derived macrophages/moncytes/CD34+ cells ex vivo. The fusion protein will be secreted and will bind to tumour cells bearing the erb-2 antigen.

Epidermal growth factor (EGF) will bind to its ligand erb-2 (an EGF receptor) thus obviating the requirement of a ScFv. Erb-2 is highly associated with tumour cells (Hynes N E Semin Cancer Biol 1993 February;4(1):19-26, Amplification and over expression of the erbB-2 gene in human tumors: its involvement in tumor development, significance as a prognostic factor, and potential as a target for cancer therapy). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to massive increase in IL-2 which promotes CD8 (cytotoxic T cell) expansion (Linsley P S, Brady W, Grosmaire L, Aruffo A, Damle N K, Ledbetter J A J Exp Med 1991 March 1;173(3):721-730 Binding of the B cell activation antigen B7 to CD28 costimulates T cell proliferation and interleukin 2 mRNA accumulation.) Tumour cells that have been B7 transfected with B7 have shown retardation in animal models (Townsend S E, Allison J P Science 1993 15;259(5093): 368-370 Tumor rejection after direct costimulation of CD8+T cells by B7-transfected melanoma cells). It is has been reported that B7 will enhance the CTL response to tumour antigens specific to tumour cells thus leading to the destruction of all such cells.

Example 15

Production of Cell Lines Expressing Fusion Constructs

The ScFv-IgG gene was excised from pBSII/L/ScFv/hIgG1 by XhoI digestion, and cloned into pLXSN via the XhoI site, to make pLXSN/ScFv-IgG, such that after chromosomal integration it is under transcriptional control of the LTR. Virus was made in the human kidney cell line 293T by co-transfecting plasmids containing the MLV gap-pol genes (PCIEGPPD) and the VSV G envelope (pRV67) using the triple plasmid HIT system (Landau & Littman 1992 J Virol 66 5110, Soneoka Y et al 1995 NAR 23:628-633). Virus is harvested after 48 hours and used to transduce BHK-21 cells (ATCC# CCL-10). Approximately 24 hours post-transduction, transduced cells are selected by the addition of 1 mg/ml G418 (Gibco BRL) to culture medium. The supernatant from positive colonies was harvested and concentrated by centrifugation through a Centriprep (Amicon, Glos. UK) 10 filter (all proteins larger than 10 kDa are purified/concentrated) and a Centricon (Amicon) 10 filter. Supernatants were concentrated approximately 30 fold.

Other fusion proteins are cloned into pLXSN via the XhoI site and expressed and concentrated using a similar protocol.

FACS analysis of fusion protein binding with cells expressing specific ligand To determine if the ScFv-IgG fusion protein is specific for its antigen, human 5T4, FACS analysis of a human bladder carcinoma tumour line (EJ) or a stable murine cell line expressing h5T4, A9-h5T4 (Myers et al 1994 JBC) and a 5T4 negative line A9-neo was carried out. Approximately 5×10$^5$ A9 or EJ cells, in a round bottom 96 well plate (Falcon) were incubated with 100 ul of a 1:5 dilution of concentrated supernatant (as described above) for 1 hour at 4 oC. After washing, bound protein is detected using an anti human IgG/FITC conjugated antibody (Dako). Cells were analysed on a Becton Dickinson FACS machine. FACS results show that there is at least a 1 log shift in fluorescence activity in those 5T4 positive cells treated with the ScFv-IgG construct compared to the negative control construct consisting of the ScFv protein alone. A9 neo FACS shows that there is no non-specific binding of the ScFv component of the fusion protein.

FACS analysis of ScFv-IgE is carried out similar to above except that anti-human IgE-FITC (Dako) is used to detect binding of the fusion protein.

The B7/EGF fusion protein is analysed for binding using FACS and HC11-erb-2 positive cells (Hynes et al 1990). CTLA4-Ig (Ancell, USA) is used to analyse the bioactivity of the B7 component of the bound fusion protein. Antimouse IgG-FITC is used to show CTLA-4 binding.

Example 16

Assembly and Cloning of an ScFv Specific for IL-5

The anti-IL-5 scFv is assembled by RT-PCR using material prepared from a hybridoma line such as the one expressing the humanised Mab to IL-5, SB 240563 (Leckie, M J, Am. J. Respir. Crit. Care Med. 159, A624 1999). Techniques are similar to those described by Clackson et al (Genetically engineered monoclonal antibodies. Br J Rheumatol. 1991;30 Suppl 2:36-9). Briefly, total RNA is prepared from SB 240563 cells. First strand synthesis is performed using MMLV reverse transcriptase using oligo dT primer. Template cDNA's are amplified by PCR with V$_H$ and V$_L$ gene specific primer pairs that include restriction enzyme sites to allow cloning into pKLink, a pBluescript II SK (pBSII) plasmid that contains a flexible linker sequence, wherein the linker is three copies of the amino-acid sequence gly-gly-gly-gly-ser (SEQ ID NO:28) (FIG. 5). This forms the single chain antibody cDNA (FIG. 6). A double stranded oligonucleotide encoding a translation initiation, Kozak sequence and the human 1 g kappa light chain signal peptide for secretion, is then cloned upstream of the scFv.

The whole construct is then excised with SbfI and EcoRI and cloned into pONY 8.1SM (see WO 01/36486) (FIG. 7).

Cloning of scFv Specific for IL-5 into pAdApt

The L-scFv cloned into pBSII is digested with XbaI, filled in to give a blunt end and then digested with EcoRI. The pAdApt vector is digested with HindIII filled in to give a blunt end and then digested EcoRI. The two molecules are then ligated to give a recombinant transfer vector.

Production of Recombinant Adenovirus Expressing the scFv Fusion Construct

To produce recombinant adenovirus expressing the scFv fusion construct, PerC6 cells are transfected with equimolar amounts of the recombinant transfer vector containing the fusion construct and an adenovirus Genome vector (AdEasy from Quantum Apligene, Harefield UK). Recombinant virus is then harvested as described in the Crucell protocol.

The recombinant virus can be used as a pharmaceutical composition for the prevention and/or treatment of asthma.

Example 17

Assembly and Cloning of an ScFv Specific for the Envelope Protein gp120 of HIV

The anti-HIV scFv is assembled by RT-PCR using material prepared from a hybridoma line expressing a mAb to the envelope protein gp120 of HIV, such as mAb 110.3 (Conelly et al, Virology 295: 554-557, 1994.). Alternatively guided selection is used to make a humanised antibody (see Beiboer S H et al, *J Mol Biol*, 2000; 296:833-849) from which the scFv is then derived. Techniques are similar to that described by Clackson et al (Genetically engineered monoclonal antibodies. Br J. Rheumatol. 1991;30 Suppl 2:36-9). Briefly, total RNA is prepared from the hybridoma cells. First strand synthesis is performed using MMLV reverse transcriptase using oligo dT primer. Template cDNA's are amplified by PCR with V$_H$ and V$_L$ gene specific primer pairs that include restriction enzyme sites, such as those shown below, to allow cloning into pKLink, a pBluescript II SK (pBSII) plasmid that contains a flexible linker sequence, wherein the linker is three copies of the amino-acid sequence gly-gly-gly-gly-ser (SEQ ID NO:28) (FIG. 5). This forms the single chain antibody cDNA (FIG. 21). A double stranded oligonucleotide encoding a translation initiation, Kozak sequence and the human 1 g kappa light chain signal peptide for secretion, is then cloned upstream of the scFv.

The whole construct is then excised with SbfI and EcoRI and cloned into pONY 8.1SM (FIG. 8).

Cloning of scFv Specific for the Envelope Protein gp120 of HIV

The L-scFv cloned into pBSII is digested with XbaI, filled in to give a blunt end and then digested with EcoRI. The pAdApt vector is digested with HindIII filled in to give a blunt end and then digested EcoRI The two molecules are then ligated to give a recombinant transfer vector.

To produce recombinant adenovirus expressing the scFv fusion constructs, PerC6 cells are transfected with equimolar amounts of the recombinant transfer vector containing the fusion construct and an adenovirus Genome vector (AdEasy from Quantum Apligene, Harefield UK). Recombinant virus is then harvested as described in the Crucell protocol.

The recombinant virus can be used to enhance a patient's anti-HIV response by providing an in vivo factory for a gp120-specific antibody.

Example 18

Anti-TNF Antibodies and Rheumatoid Arthritis

Assembly and Cloning of scFv Specific for Human TNF

The recombinant human anti-TNF antibodies are isolated as described in Hoogenboom et al. (Human antibodies that bind human TNF alpha. U.S. Pat. No. 4,090,382) Below is described ian example based on the antibody D2E7. Template cDNA's are amplified by PCR with V$_H$ and V$_L$ gene specific primer pairs that include restriction enzyme sites, such as those shown below, to allow cloning into pKLink, a pBluescript II SK (pBSII) plasmid that contains a flexible linker sequence, wherein the linker is three copies of the amino-acid secluence gly-gly-gly-gly-ser (SEQ ID NO:28) (FIG. 5). This forms the single chain antibody cDNA (FIG. 6). A double stranded oligonucleotide encoding a translation initiation, Kozak sequence and the human Ig kappa light chain signal peptide for secretion, similar to that described in the construction of the scFv to 5T4 (see WO 01/36486), is then cloned upstream of the scFv (FIG. 6).

The whole construct can then be excised with SbfI and EcoRI and cloned into a lentivector such as pONY 8.1SM (FIG. 9).

In this example the VH is amplified with additional SpeI and MfeI restriction sites at the 5' end and an additional AgeI site at the 3' end. The SpeI and AgeI sites are used to clone into pKlink. The VL is amplified with an additional BamHI restriction site at the 5' end and an additional EcoRI site at the 3'end, which are used for cloning into pKlink.

The leader signal peptide is synthesised as two complementary oligonucleotides, that are annealed to give restriction enzyme overhangs and then cloned as a double stranded oligonucleotide between the SpeI and MfeI sites at the 5' end of the scFv cDNA.

The Kozak sequence including the ATG start codon (underlined) is in bold and italics.

The $V_H$ and $V_L$ sequences are shown as SEQ ID NOs 8 and 9 respectively.

The recombinant virus can be used as a pharmaceutical composition for the prevention and/or treatment of arthritis.

Example 19

Retina Disease

Assembly and Cloning of scFv Specific for Human VEGF

The recombinant human anti-VEGF antibodies are isolated as described in Vitaliti et al Cancer Res 2000 August 15;60(16):4311-4. (Inhibition of tumor angiogenesis by a single-chain antibody directed against vascular endothelial growth factor). Below is described an example based on the antibody sequence available in the GenBank database (submitted by Yan et al; accession no. AB014341). Template cDNA's are amplified by PCR with $V_H$ and $V_L$ gene specific primer pairs that include restriction enzyme sites, such as those shown below, to allow cloning into pKLink, a pBluescript II SK (pBSII) plasmid that contains a flexible linker sequence, wherein the linker is three copies of the amino-acid gly-gly-gly-gly-ser (SEQ ID NO:28) (FIG. 5). This forms the single chain antibody cDNA (FIG. 6). A double stranded oligonucleotide encoding a translation initiation, Kozak sequence and the human 1 g kappa light chain signal peptide for secretion, similar to that described in the construction of the scFv to 5T4 (see WO 01/36486), is then cloned upstream of the scFv (FIG. 6).

The whole construct is then be excised with SbfI and EcoRI and cloned into a lentivector such as pONY 8.1SM (FIG. 10).

In this example the VH is amplified with additional SpeI and MfeI restriction sites at the 5' end and-an additional AgeI site at the 3' end. The SpeI and AgeI sites are used to clone into pKlink. The VL is amplified with an additional BamHI restriction site at the 5' end and an additional EcoRI site at the 3'end, which are used for cloning into pKlink.

The leader signal peptide is synthesised as two complementary oligonucleotides, that are annealed to give restriction enzyme overhangs and then cloned as a double stranded oligonucleotide between the SpeI and MfeI sites at the 5' end of the scFv cDNA.

The Kozak sequence including the ATG start codon (underlined) is in bold and italics.

The ScFv sequence is shown as SEQ ID NO:10.

The recombinant virus can be used as a pharmaceutical composition for the prevention and/or treatment of arthritis.

Example 20

Gene Transfer of scFv Proteins In Vivo

The aim of this study was to verify the expression of scFv following intratumour administration of a viral vector encoding scFv that has been tagged with myc and His polypeptides.

Experimental Design

An adenoviral vector expressing murine B7.1 fused to scFvmycHis (AdB7-scFv) was used to demonstrate the intra-tumoural delivery of genes that encode for scFv proteins specific to 5T4. A control adenoviral vector expressing the lac z gene (Adlac z) was also used. Both vectors used were of the human Ad5 serotype that lacks the genes encoding for E1 and E3.

CT26 cells expressing h5T4 (CT26-h5T4) were washed twice in PBS and $5 \times 10^5$ cells were injected sc into both flanks of a female Balb/c mouse. Each tumour was established to an average diameter of 5 mm and received 3 daily injections of $4 \times 10^8$ pfu Adenovirus in 50 µl. 48 hours after the final injection tumours were excised and snap frozen and 100 µm sections were cut prior to staining for murine B7.1 or c-myc proteins.

Results

There was no positive staining for c-myc or B7.1 in sections adjacent to those that were positive for lac z (FIG. 11). This confirms the specificity of staining by the antibodies used and also verifies that B7.1 positive staining seen is due to gene transfer of the scFv fusion protein and not the presence of adenovirus.

Gene transfer of B7-scFv was verified on adjacent sections that stained positive for B7.1 as well as for the c-myc tag (FIG. 12). Specificity of staining was verified by the absence of positive cells in those sections that were incubated in the secondary antibody alone.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for inhibiting the growth of a tumor in a mammal comprising delivering directly to the tumor a vector comprising a polynucleotide sequence which encodes and expresses a fusion protein comprising (a) an antibody that specifically binds to a surface antigen on the tumor; and (b) an antitumor protein, wherein the fusion protein is secreted and the antitumor protein is expressed in cells of the tumor thereby inhibiting the growth of the tumor.

2. The method of claim 1, wherein the antitumor protein is selected from the group consisting of an enzyme, a pro-drug activating enzyme, a toxin, all or part of a cytokine, an effector domain from an immunoglobulin heavy chain, and a domain which activates macrophage FcgR I, II, or III receptors.

3. A method for inhibiting the growth of a tumor in a mammal comprising delivering directly to the tumor a vector comprising a polynucleotide sequence which encodes and expresses a fusion protein comprising (a) an antibody that specifically binds to a surface antigen on the tumor; and (b) an antitumor protein, wherein the fusion protein comprises a signal peptide, and wherein the antitumor protein is expressed in cells of the tumor thereby inhibiting the growth of the tumor.

4. The method of claim 1 wherein said vector is a viral vector.

5. The method of claim 1 wherein said vector is a non-viral vector.

6. The method of claim 4 wherein the vector is a retroviral vector.

7. The method of claim 6 wherein the vector is lentiviral vector.

8. The method of claim 4 wherein the vector is pseudotyped.

9. The method of claim 6 wherein the vector is pseudotyped.

10. The method of claim 7 wherein the vector is pseudotyped.

11. The method of claim 1, wherein the antitumor protein comprises a domain which confers protein stability.

12. The method of claim 3 wherein the vector is a viral vector.

13. The method of claim 3 wherein the vector is a non-viral vector.

14. The method of claim 12 wherein the vector is a retroviral vector.

15. The method of claim 14 wherein the vector is lentiviral vector.

16. The method of claim 12 wherein the vector is pseudotyped.

17. The method of claim 14 wherein the vector is pseudotyped.

18. The method of claim 15 wherein the vector is pseudotyped.

* * * * *

SEQUENCE LISTING

<160> NUMBER OF SEQ ID NOS: 27

<210> SEQ ID NO 1
<211> LENGTH: 729

<212> TYPE: DNA
<213> ORGANISM: Artificial Sequence
<220> FEATURE:
<223> OTHER INFORMATION: 5T4 ScFv

<400> SEQUENCE: 1

```
gaggtccagc ttcagcagtc tggacctgac ctggtgaagc ctggggcttc agtgaagata      60
tcctgcaagg cttctggtta ctcattcact ggctactaca tgcactgggt gaagcagagc     120
catggaaaga gccttgagtg gattggacgt attaatccta caatggtgt tactctctac      180
aaccagaaat tcaaggacaa ggccatatta actgtagaca agtcatccac acagcctac     240
atggagctcc gcagcctgac atctgaggac tctgcggtct attactgtgc aagatctact     300
atgattacga actatgttat ggactactgg ggtcaagtaa cctcagtcac cgtctcctca     360
ggtggtggtg ggagcggtgg tggcggcact ggcggcggcg atctagtat tgtgatgacc      420
cagactccca cattcctgct tgtttcagca ggagacaggg ttaccataac ctgcaaggcc     480
agtcagagtg tgagtaatga tgtagdttgg taccaacaga gccagggca gtctcctaca     540
ctgctcatat cctatacatc cagtcgctac gctggagtcc ctgatcgctt cattggcagt     600
ggatatggga cggatttcac tttcaccatc agcactttgc aggctgaaga cctggcagtt     660
tatttctgtc agcaagatta taattctcct ccgacgttcg gtggaggcac caagctggaa     720
atcaaacgg                                                              729
```

<210> SEQ ID NO 2
<211> LENGTH: 1807
<212> TYPE: DNA
<213> ORGANISM: Artificial Sequence
<220> FEATURE:
<223> OTHER INFORMATION: 5T4Sab1

<400> SEQUENCE: 2

```
aagcttccac catgggatgg agctgtatca tcctcttctt ggtagcaaca gctacaggtg      60
tccactccga ggtccagctt cagcagtctg gacctgacct ggtgaagcct ggggcttcag     120
tgaagatatc ctgcaaggct tctggttact cattcactgg ctactacatg cactgggtga     180
agcagagcca tggaaagagc cttgagtgga ttggacgtat taatcctaac aatggtgtta     240
ctctctacaa ccagaaattc aaggacaagg ccatattaac tgtagacaag tcatccacca     300
cagcctacat ggagctccgc agcctgacat ctgaggactc tgcggtctat tactgtgcaa     360
gatctactat gattacgaac tatgttatgg actactgggg tcaagtaacc tcagtcaccg     420
tctcctcagg tggtggtggg agcggtggtg gcggcactgg cggcggcgga tctagtattg     480
tgatgaccca gactcccaca ttcctgcttg tttcagcagg agacagggtt accataacct     540
gcaaggccag tcagagtgtg agtaatgatg tagcttggta ccaacagaag ccagggcagt     600
ctcctacact gctcatatcc tatacatcca gtcgctacgc tggagtccct gatcgcttca     660
ttggcagtgg atatgggacg gatttcactt tcaccatcag cactttgcag gctgaagacc     720
tggcagttta tttctgtcag caagattata attctcctcc gacgttcggt ggaggcacca     780
agctggaaat caaacgggcc tccaccaagg gcccatcggt cttccccctg gcaccctcct     840
ccaagagcac ctctggggc acagcggccc tgggctgcct ggtcaaggac tacttccccg     900
aaccggtgac ggtgtcgtgg aactcaggcg ccctgaccag cggcgtgcac accttcccgg     960
ctgtcctaca gtcctcagga ctctactccc tcagcagcgt ggtgaccgtg ccctccagca    1020
gcttgggcac ccagacctac atctgcaacg tgaatcacaa gcccagcaac accaaggtgg    1080
```

```
acaagaaagt tgagcccaaa tcttgtgaca aaactcacac atgcccaccg tgcccagcac    1140
ctgaactcct gggggggaccg tcagtcttcc tcttccccccc aaaacccaag gacaccctca   1200
tgatctcccg gacccctgag gtcacatgcg tggtggtgga cgtgagccac gaagaccctg    1260
aggtcaagtt caactggtac gtggacggcg tggaggtgca taatgccaag acaaagccgc    1320
gggaggagca gtacaacagc acgtaccgtg tggtcagcgt cctcaccgtc ctgcaccagg    1380
actggctgaa tggcaaggag tacaagtgca aggtctccaa caaagccctc ccagccccca   1440
tcgagaaaac catctccaaa gccaagggc agccccgaga accacaggtg tacaccctgc     1500
ccccatcccg ggatgagctg accaagaacc aggtcagcct gacctgcctg gtcaaaggct    1560
tctatcccag cgacatcgcc gtggagtggg agagcaatgg gcagccggag aacaactaca    1620
agaccacgcc tcccgtgctg gactccgacg gctccttctt cctctacagc aagctcaccg    1680
tggacaagag caggtggcag caggggaacg tcttctcatg ctccgtgatg catgaggctc    1740
tgcacaacca ctacacgcag aagagcctct ccctgtctcc gggtaaatga gtgcgacggc    1800
caagctt                                                              1807
```

<210> SEQ ID NO 3
<211> LENGTH: 1467
<212> TYPE: DNA
<213> ORGANISM: Artificial Sequence
<220> FEATURE:
<223> OTHER INFORMATION: B7-1.5T4.1

<400> SEQUENCE: 3

```
atgggccaca cacggaggca gggaacatca ccatccaagt gtccataccct caatttcttt     60 cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaggagaag aaaatggtgc tgactatgat gtctggggac     240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagtttcc caagatcctg aaactgagct ctatgctgtt    600
agcagcaaac tggatttcaa tatgacaacc aaccacagct tcatgtgtct catcaagtat    660
ggacatttaa gagtgaatca gaccttcaac tggaatacaa ccaagcaaga gcattttcct    720
gatggaggcg ggggatccga ggtccagctt cagcagtctg gacctgacct ggtgaagcct    780
ggggcttcag tgaagatatc ctgcaaggct tctggttact cattcactgg ctactacatg    840
cactgggtga agcagagcca tggaaagagc cttgagtgga ttggacgtat taatcctaac    900
aatggtgtta ctctctacaa ccagaaattc aaggacaagg ccatattaac tgtagacaag    960
tcatccacca cagcctacat ggagctccgc agcctgacat ctgaggactc tgcggtctat    1020
tactgtgcaa gatctactat gattacgaac tatgttatgg actactgggg tcaagtaacc    1080
tcagtcaccg tctcctcagg tggtggtggg agcggtggtg gcggcactgg cggcggcgga    1140
tctagtattg tgatgaccca gactcccaca ttcctgcttg tttcagcagg agacagggtt    1200
accataacct gcaaggccag tcagagtgtg agtaatgatg tagcttggta ccaacagaag    1260
ccagggcagt ctcctacact gctcatatcc tatacatcca gtcgctacgc tggagtccct    1320
```

```
gatcgcttca ttggcagtgg atatgggacg gatttcactt tcaccatcag cactttgcag    1380
gctgaagacc tggcagttta tttctgtcag caagattata attctcctcc gacgttcggt    1440
ggaggcacca agctggaaat caaataa                                        1467

<210> SEQ ID NO 4
<211> LENGTH: 738
<212> TYPE: DNA
<213> ORGANISM: Artificial Sequence
<220> FEATURE:
<223> OTHER INFORMATION: B7-2(1-241)

<400> SEQUENCE: 4
atgggactga gtaacattct ctttgtgatg gccttcctgc tctctggtgc tgctcctctg      60
aagattcaag cttatttcaa tgagactgca gacctgccat gccaatttgc aaactctcaa    120
aaccaaagcc tgagtgagct agtagtattt tggcaggacc aggaaaactt ggttctgaat    180
gaggtatact taggcaaaga gaaatttgac agtgttcatt ccaagtatat gggccgcaca    240
agttttgatt cggacagttg gaccctgaga cttcacaatc ttcagatcaa ggacaagggc    300
ttgtatcaat gtatcatcca tcacaaaaag cccacaggaa tgattcgcat ccaccagatg    360
aattctgaac tgtcagtgct tgctaacttc agtcaacctg aaatagtacc aatttctaat    420
ataacagaaa atgtgtacat aaatttgacc tgctcatcta tacacggtta cccagaacct    480
aagaagatga gtgttttgct aagaaccaag aattcaacta tcgagtatga tggtattatg    540
cagaaatctc aagataatgt cacagaactg tacgacgttt ccatcagctt gtctgtttca    600
ttccctgatg ttacgagcaa tatgaccatc ttctgtattc tggaaactga caagacgcgg    660
cttttatctt caccttttctc tatagagctt gaggaccctc agcctccccc agaccacatt    720
cctggaggcg ggggatcc                                                   738

<210> SEQ ID NO 5
<211> LENGTH: 1518
<212> TYPE: DNA
<213> ORGANISM: Artificial Sequence
<220> FEATURE:
<223> OTHER INFORMATION: B7 link ScFv sequence

<400> SEQUENCE: 5
atggcttgca attgtcagtt gatgcaggat acaccactcc tcaagtttcc atgtccaagg     60
ctcattcttc tctttgtgct gctgattcgt ctttcacaag tgtcttcaga tgttgatgaa    120
caactgtcca agtcagtgaa agataaggta ttgctgcctt gccgttacaa ctctccgcat    180
gaagatgagt ctgaagaccg aatctactgg caaaaacatg acaaagtggt gctgtctgtc    240
attgctggga aactaaaagt gtggcccgag tataagaacc ggactttata tgacaacact    300
acctactctc ttatcatcct gggcctggtc ctttcagacc ggggcacata cagctgtgtc    360
gttcaaaaga aggaaagagg aacgtatgaa gttaaacact ggctttagt aaagttgtcc    420 atcaaagctg acttctctac ccccaacata actgagtctg aaacccatc tgcagacact    480 aaaaggatta cctgctttgc ttccgggggt ttcccaaagc ctcgcttctc ttggttggaa    540
aatggaagag aattacctgg catcaatacg acaatttccc aggatcctga atctgaattg    600
tacaccatta gtagccaact agatttcaat acgactcgca ccacaccat aagtgtctc     660 attaaatatg gagatgctca cgtgtcagag acttcacct gggaaaaacc cccagaagac    720
cctcctgata gcaagcccgg gggtggtggg agcggtggtg gcggcagtgg cggcggcgga    780
```

-continued

```
actagtgagg tccagcttca gcagtctgga cctgacctgg tgaagcctgg ggcttcagtg       840
aagatatcct gcaaggcttc tggttactca ttcactggct actacatgca ctgggtgaag       900
cagagccatg gaaagagcct tgagtggatt ggacgtatta atcctaacaa tggtgttact       960
ctctacaacc agaaattcaa ggacaaggcc atattaactg tagacaagtc atccaccaca      1020
gcctacatgg agctccgcag cctgacatct gaggactctg cggtctatta ctgtgcaaga      1080
tctactatga ttacgaacta tgttatggac tactggggtc aagtaacttc agtcaccgtc      1140
tcttcaggtg gtggtgggag cggtggtggc ggcactggcg gcggcggatc tagtattgtg      1200
atgacccaga ctcccacatt cctgcttgtt tcagcaggac agggttac ataacctgc         1260 aaggccagtc agagtgtgag taatgatgta gcttggtacc aacagaagcc agggcagtct      1320
cctacactgc tcatatccta tacatccagt cgctacgctg gagtccctga tcgcttcatt      1380
ggcagtggat atgggacgga tttcactttc accatcagca ctttgcaggc tgaagacctg      1440
gcagtttatt tctgtcagca agattataat tctcctccga cgttcggtgg aggcaccaag      1500
ctggaaatca aacggtaa                                                    1518

<210> SEQ ID NO 6
<211> LENGTH: 2090
<212> TYPE: DNA
<213> ORGANISM: Artificial Sequence
<220> FEATURE:
<223> OTHER INFORMATION: 5T4 ScFv - human IgE fusion

<400> SEQUENCE: 6
ctcgagccac catgggatgg agctgtatca tcctcttctt ggtagcaaca gctacaggtg        60
tccactccga ggtccagctg cagcagtctg gacctgacct ggtgaagcct ggggcttcag      120
tgaagatatc ctgcaaggct tctggttact cattcactgg ctactacatg cactgggtga      180
agcagagcca tggaaagagc cttgagtgga ttggacgtat taatcctaac aatggtgtta      240
ctctctacaa ccagaaattc aaggacaagg ccatattaac tgtagacaag tcatccacca      300
cagcctacat ggagctccgc agcctgacat ctgaggactc tgcggtctat tactgtgcaa      360
gatctactat gattacgaac tatgttatgg actactgggg tcaagtaact tcagtcaccg      420
tctcttcagg tggtgtggg agcggtggtg gcggcactgg cggcggcgga tctagtattg       480
tgatgaccca gactcccaca ttcctgcttg tttcagcagg acagggtt accataaccct       540 gcaaggccag tcagagtgtg agtaatgatg tagcttggta ccaacagaag ccagggcagt      600
ctcctacact gctcatatcc tatacatcca gtcgctacgc tggagtccct gatcgcttca      660
ttggcagtgg atatgggacg gatttcactt tcaccatcag cactttgcag gctgaagacc      720
tggcagttta tttctgtcag caagattata attctcctcc gacgttcggt ggaggcacca      780
agcttgaaat caaacgggcc tccacacaga gcccatccgt cttcccctg acccgctgct        840 gcaaaaacat tccctccaat gccacctccg tgactctggg ctgcctggcc acgggctact      900
tcccggagcc ggtgatggtg acctgggaca caggctccct caacgggaca actatgacct      960
taccagccac caccctcacg ctctctggtc actatgccac catcagcttg ctgaccgtct     1020
cgggtgcgtg gccaagcag atgttcacct gccgtgtggc acacactcca tcgtccacag      1080
actgggtcga acaaaaacc ttcagcgtct gctccaggga cttcaccccg ccaccgtga       1140 agatcttaca gtcgtcctgc gacggcggcg ggcacttccc ccgaccatc cagctcctgt      1200 gcctcgtctc tgggtacacc ccagggacta tcaacatcac ctggctggag gacgggcagg      1260
tcatggacgt ggacttgtcc accgcctcta ccacgcagga gggtgagctg gcctccacac      1320
```

```
aaagcgagct caccctcagc cagaagcact ggctgtcaga ccgcacctac acctgccagg    1380
tcacctatca aggtcacacc tttgaggaca gcaccaagaa gtgtgcagat ccaacccga    1440 gagggtgag cgcctaccta agccggccca gcccgttcga cctgttcatc cgcaagtcgc    1500
ccacgatcac ctgtctggtg gtggacctgg cacccagcaa ggggaccgtg aacctgacct    1560
ggtcccgggc cagtgggaag cctgtgaacc actccaccag aaaggaggag aagcagcgca    1620
atggcacgtt aaccgtcacg tccaccctgc cggtgggcac ccgagactgg atcgagggg    1680 agacctacca gtgcagggtg acccaccccc acctgcccag ggccctcatg cggtccacga    1740
ccaagaccag cggcccgcgt gctgccccgg aagtctatgc gtttgcgacg ccggagtggc    1800
cggggagccg ggacaagcgc accctcgcct gcctgatcca gaacttcatg cctgaggaca    1860
tctcggtgca gtggctgcac aacgaggtgc agctcccgga cgcccggcac agcacgacgc    1920
agccccgcaa gaccagggc tccggcttct tcgtcttcag ccgcctggag gtgaccaggg    1980
ccgaatggga gcagaaagat gagttcatct gccgtgcagt ccatgaggca gcgagcccct    2040
cacagaccgt ccagcgagcg gtgtctgtaa atcccggtaa atgagagctc    2090

<210> SEQ ID NO 7
<211> LENGTH: 945
<212> TYPE: DNA
<213> ORGANISM: Artificial Sequence
<220> FEATURE:
<223> OTHER INFORMATION: B7-EGF fusion

<400> SEQUENCE: 7
atggcttgca attgtcagtt gatgcaggat acaccactcc tcaagtttcc atgtccaagg     60
ctcattcttc tctttgtgct gctgattcgt ctttcacaag tgtcttcaga tgttgatgaa    120
caactgtcca agtcagtgaa agataaggta ttgctgcctt gccgttacaa ctctccgcat    180
gaagatgagt ctgaagaccg aatctactgg caaaaacatg acaaagtggt gctgtctgtc    240
attgctggga aactaaaagt gtggcccgag tataagaacc ggactttata tgacaacact    300
acctactctc ttatcatcct gggcctggtc ctttcagacc ggggcacata cagctgtgtc    360
gttcaaaaga aggaaagagg aacgtatgaa gttaaacact ggctttagt aaagttgtcc    420 atcaaagctg acttctctac ccccaacata actgagtctg aaacccatc tgcagacact    480 aaaaggatta cctgctttgc ttccgggggt ttcccaaagc ctcgcttctc ttggttggaa    540
aatggaagag aattacctgg catcaatacg acaatttccc aggatcctga atctgaattg    600
tacaccatta gtagccaact agatttcaat acgactcgca accacaccat taagtgtctc    660
attaaatatg gagatgctca cgtgtcagag gacttcacct gggaaaaacc cccagaagac    720
cctcctgata gcaagcccgg gggtggtggg agcggtggtg gcggcagtgg cggcggcgga    780
actagtaata gtgactctga atgtcccctg tcccacgatg gtactgcct ccatgatggt    840 gtgtgcatgt atattgaagc attggacaag tatgcatgca actgtgttgt tggctacatc    900
ggggagcgat gtcagtaccg agacctgaag tggtgggaac tgcgc                    945

<210> SEQ ID NO 8
<211> LENGTH: 363
<212> TYPE: DNA
<213> ORGANISM: Artificial Sequence
<220> FEATURE:
<223> OTHER INFORMATION: Anti-TNF alpha VH

<400> SEQUENCE: 8
```

```
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tgagggccg attcaccatc tccagagaca acgccaagaa ctccctgtat      240
ctgcaaatga acagtctgag agctgaggat acggccgtat attactgtgc gaaagtctcg     300
taccttagca ccgcgtcctc ccttgactat tggggccaag taccctggt caccgtctcg      360 agt                                                                    363

<210> SEQ ID NO 9
<211> LENGTH: 321
<212> TYPE: DNA
<213> ORGANISM: Artificial Sequence
<220> FEATURE:
<223> OTHER INFORMATION: Anti-TNF alpha VJ

<400> SEQUENCE: 9
gacatcgtga tgacccagtc tccatcctcc ctgtctgcat ctataggga cagagtcacc       60 atcacttgtc gggaaagtca gggcatcaga aatgatttag ctggtatca gcagaaacca     120 gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttactt ttgtcaacag gctaacagtc ccctcccac tttcggcgga      300 gggaccaagg tggaaatcaa a                                                321

<210> SEQ ID NO 10
<211> LENGTH: 789
<212> TYPE: DNA
<213> ORGANISM: Artificial Sequence
<220> FEATURE:
<223> OTHER INFORMATION: Anti-VEGF ScFv

<400> SEQUENCE: 10
atggcccagg tgcagctggt gcagtctggg gctgaggtga agaagcctgg ggcctcagtg      60
aaggtttcct gcaaggcttc tggatacacc ttcactagct atgctatgca ttgggtgcgc     120
caggcccccg gacaaaggct tgagtggatg ggatggatca acgctggcaa tggtaacaca     180
aaatattcac agaagttcca gggcagagtc accattacca gggacacatc cgcgagcaca     240
gcctacatgg agctgagcag cctgagatct gaagacacgg ccgtgtatta ctgtgcaagg     300
ttgacgcgta taagtttaa gtcgcgtggt cattggggcc aagtaccct ggtcaccgtg      360 tcgagaggtg gcggtggctc gggcggtggt ggtcgggtg gcggcggatc ttctgagctg     420
actcaggacc ctgctgtgtc tgtggccttg ggacagacag tcaggatcac atgccaagga     480
gacagcctca gaagctatta tgcaagctgg taccagcaga agccaggaca ggcccctgta     540
cttgtcatct atggtaaaaa caaccggccc tcagggatcc cagaccgatt ctctggctcc     600
agctcaggaa acacagcttc cttgaccatc actgggctc aggcggaaga tgaggctgac      660
tattactgta actccgggga cagcagtggt aaccatgtgg tattcggcgg agggaccaag     720
ctgaccgtcc taggtgcggc cgcagaacaa aaactcatct cagaagagga tctgaatggg     780
gccgcatag                                                              789

<210> SEQ ID NO 11
<211> LENGTH: 69
<212> TYPE: DNA
<213> ORGANISM: Artificial Sequence
```

```
<220> FEATURE:
<223> OTHER INFORMATION: Translation initiation signal

<400> SEQUENCE: 11
aagcttccac ccatgggatg gagctgtatc atcctcttct tggtagcaac agctacaggt      60
gtccactcc                                                             69

<210> SEQ ID NO 12
<211> LENGTH: 43
<212> TYPE: DNA
<213> ORGANISM: Artificial Sequence
<220> FEATURE:
<223> OTHER INFORMATION: Oligonucleotide used to make flexible linker

<400> SEQUENCE: 12
gggggtggtg ggagcggtgg tggcggcagt ggcggcggcg gaa                       43

<210> SEQ ID NO 13
<211> LENGTH: 47
<212> TYPE: DNA
<213> ORGANISM: Artificial Sequence
<220> FEATURE:
<223> OTHER INFORMATION: Oligonucleotide used to make flexible linker

<400> SEQUENCE: 13
ctagttccgc cgccgccact gccgccacca ccgctcccac caccccc                   47

<210> SEQ ID NO 14
<211> LENGTH: 38
<212> TYPE: DNA
<213> ORGANISM: Artificial Sequence
<220> FEATURE:
<223> OTHER INFORMATION: Forward primer used in Example 10

<400> SEQUENCE: 14
ctcgaattcc accatggctt gcaattgtca gttgatgc                             38

<210> SEQ ID NO 15
<211> LENGTH: 30
<212> TYPE: DNA
<213> ORGANISM: Artificial Sequence
<220> FEATURE:
<223> OTHER INFORMATION: Reverse primer used in Example 10

<400> SEQUENCE: 15
ctccccgggc ttgctatcag gagggtcttc                                      30

<210> SEQ ID NO 16
<211> LENGTH: 29
<212> TYPE: DNA
<213> ORGANISM: Artificial Sequence
<220> FEATURE:
<223> OTHER INFORMATION: Forward primer used in Example 10

<400> SEQUENCE: 16
ctcactagtg aggtccagct tcagcagtc                                       29

<210> SEQ ID NO 17
<211> LENGTH: 44
<212> TYPE: DNA
<213> ORGANISM: Artificial Sequence
<220> FEATURE:
<223> OTHER INFORMATION: Reverse primer used in Example 10

<400> SEQUENCE: 17
```

```
ctcgcggccg cttaccgttt gatttccagc ttggtgcctc cacc                44
```

<210> SEQ ID NO 18
<211> LENGTH: 87
<212> TYPE: DNA
<213> ORGANISM: Artificial Sequence
<220> FEATURE:
<223> OTHER INFORMATION: Oligonucleotide used in Example 12

<400> SEQUENCE: 18

```
ctagactcga gccaccatgg gatggagctg tatcatcctc ttcttggtag caacagctac    60
aggtgtccac tccgaggtcc agctgca                                       87
```

<210> SEQ ID NO 19
<211> LENGTH: 79
<212> TYPE: DNA
<213> ORGANISM: Artificial Sequence
<220> FEATURE:
<223> OTHER INFORMATION: Oligonucleotide used in Example 12

<400> SEQUENCE: 19

```
gctggacctc ggagtggaca cctgtagctg ttgctaccaa gaagaggatg atacagctcc    60
atcccatggt ggctcgagt                                                79
```

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide used in Example 12

<400> SEQUENCE: 20

```
gtccagctgc agcagtctgg                                               20
```

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide used in Example 12

<400> SEQUENCE: 21

```
cgtttgattt caagcttggt gc                                            22
```

<210> SEQ ID NO 22
<211> LENGTH: 40
<212> TYPE: DNA
<213> ORGANISM: Artificial Sequence
<220> FEATURE:
<223> OTHER INFORMATION: Oligonucleotide used in Example 12

<400> SEQUENCE: 22

```
gcgcaagctt gaaatcaaac gggcctccac caagggccca                         40
```

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide used in Example 12

<400> SEQUENCE: 23

```
gcgcctcgag tcatttaccc ggagacaggg                                    30
```

-continued

```
<210> SEQ ID NO 24
<211> LENGTH: 40
<212> TYPE: DNA
<213> ORGANISM: Artificial Sequence
<220> FEATURE:
<223> OTHER INFORMATION: Oligonucleotide used in Example 13

<400> SEQUENCE: 24
gcgcaagctt gaaatcaaac gggcctccac acagagccca                40

<210> SEQ ID NO 25
<211> LENGTH: 31
<212> TYPE: DNA
<213> ORGANISM: Artificial Sequence
<220> FEATURE:
<223> OTHER INFORMATION: Oligonucleotide used in Example 13

<400> SEQUENCE: 25
gcgcctcgag tcatttaccg ggatttacag a                         31

<210> SEQ ID NO 26
<211> LENGTH: 29
<212> TYPE: DNA
<213> ORGANISM: Artificial Sequence
<220> FEATURE:
<223> OTHER INFORMATION: Oligonucleotide used in Example 14

<400> SEQUENCE: 26
ggactagtaa tagtgactct gaatgtccc                            29

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide used in Example 14

<400> SEQUENCE: 27
attagcggcc gcttagcgca gttcccacca ctt                       33
```